US012740868B2

(12) United States Patent
Richter et al.

(10) Patent No.: US 12,740,868 B2
(45) Date of Patent: Sep. 22, 2026

(54) MEDIALLY STABILISING KNEE ENDOPROSTHESIS

(71) Applicant: Aesculap AG, Tuttlingen (DE)

(72) Inventors: Berna Richter, Muehlheim (DE); Brigitte Altermann, Tuttlingen (DE); Thomas Grupp, Denkingen (DE); Rachel Lang, Chaumont (FR); Alexis Vouaux, Poulangy (FR); Steeven Blanc, Chaumont (FR)

(73) Assignee: Aesculap AG, Tuttlingen (DE)

( * ) Notice: Subject to any disclaimer, the term of this patent is extended or adjusted under 35 U.S.C. 154(b) by 309 days.

(21) Appl. No.: 18/292,095

(22) PCT Filed: Jul. 20, 2022

(86) PCT No.: PCT/EP2022/070351
§ 371 (c)(1),
(2) Date: Jan. 25, 2024

(87) PCT Pub. No.: WO2023/006545
PCT Pub. Date: Feb. 2, 2023

(65) Prior Publication Data

US 2025/0090335 A1 Mar. 20, 2025

(30) Foreign Application Priority Data

Jul. 28, 2021 (DE) ..................... 10 2021 119 663.9

(51) Int. Cl.
*A61F 2/38* (2006.01)
*A61F 2/28* (2006.01)
(Continued)

(52) U.S. Cl.
CPC .......... *A61F 2/3854* (2013.01); *A61F 2/3859* (2013.01); *A61F 2/3886* (2013.01); *A61F 2/389* (2013.01)

(58) Field of Classification Search
None
See application file for complete search history.

(56) References Cited

U.S. PATENT DOCUMENTS 4,207,627 A * 6/1980 Cloutier .................... A61F 2/38
623/20.21
5,964,808 A * 10/1999 Blaha .................... A61F 2/3868
623/20.28

(Continued)

FOREIGN PATENT DOCUMENTS

DE 69629531 T2 6/2004
DE 202010000037 U1 * 3/2010 ........... A61F 2/3868

(Continued)

OTHER PUBLICATIONS

Freeman et al., "The Movement of the Knee Studied by Magnetic Resonance Imaging," Clinical Orthopaedics and Related Research, May 2003, 9 pages.

(Continued)

*Primary Examiner* — Ann Hu
(74) *Attorney, Agent, or Firm* — Christopher A. Rothe; CM Law

(57) ABSTRACT

A knee endoprosthesis for total knee arthroplasty has a femur bearing surface and a tibia bearing surface. The femur bearing surface has a medial surface and a lateral surface. The tibia bearing surface has a concave medial shell and a concave lateral shell and is configured for sliding on the femur bearing surface. The medial and lateral shells form an asymmetric surface. The medial and lateral surfaces form a non-asymmetric or quasi-symmetric bearing surface. The medial and lateral surfaces coincide in an anterior femur condylar radius. The tibia bearing surface forms an anterior contour portion with an anterior point and a posterior contour portion with a posterior point. The anterior point is proximally elevated relative to the posterior point. A portion (Continued)

of the anterior portion at the medial shell forms an antero-medial apex point. An inlay can be arranged at the tibia part.

14 Claims, 9 Drawing Sheets

(51) Int. Cl.
*A61F 2/30* (2006.01)
*A61F 2/32* (2006.01)

(56) References Cited

U.S. PATENT DOCUMENTS 7,998,205 B2* 8/2011 Hagen ........................ A61F 2/38
623/20.14
8,292,964 B2* 10/2012 Walker .................. A61F 2/3859
623/20.19
8,298,288 B2* 10/2012 Walker .................. A61F 2/3886
623/20.31
8,480,754 B2* 7/2013 Bojarski ................. A61F 2/384
623/20.14
9,820,856 B2* 11/2017 Guidera .................. A61F 2/389
9,833,323 B2* 12/2017 Richter ................. A61F 2/3886
9,999,512 B2* 6/2018 Richter ................. A61F 2/3886
10,149,768 B2* 12/2018 Otto ...................... A61F 2/3886
10,413,415 B2* 9/2019 Parisi ...................... A61F 2/389
10,835,380 B2* 11/2020 Drury ................... A61F 2/3886
11,071,631 B2* 7/2021 Walker ...................... A61F 2/38
11,278,417 B2* 3/2022 White ..................... A61F 2/389
11,304,810 B2* 4/2022 Hagen ................... A61F 2/3859
12,383,407 B2* 8/2025 Parisi .................... A61F 2/3868
12,419,753 B2* 9/2025 White ..................... A61F 2/389
2011/0029091 A1* 2/2011 Bojarski ................. A61F 2/389
606/86 R
2012/0095564 A1* 4/2012 Mihalko ................... A61F 2/38
623/20.27
2012/0323335 A1* 12/2012 Parisi .................... A61F 2/3859
623/20.35
2019/0209331 A1 7/2019 Varadarajan et al.
2020/0100903 A1* 4/2020 Lenz ....................... A61F 2/389
2020/0268519 A1 8/2020 White et al.
2022/0008208 A1* 1/2022 Heldreth ................. A61F 2/389

FOREIGN PATENT DOCUMENTS

EP 0765645 B1 8/2003
EP 2323594 B1 * 4/2016 ........... A61F 2/3886
EP 3397200 B1 * 8/2023 ........... A61F 2/3886
EP 3319551 B1 * 3/2026 ............... A61F 2/38
WO 2013152341 A1 10/2013

OTHER PUBLICATIONS

Search Report received in German Application No. 10 2021 119 663.9 dated May 9, 2022, with translation, 14 pages.
Search Report received in International Application No. PCT/EP2022/070351 dated Oct. 21, 2022, with translation, 5 pages.
Office Action received in Japanese Application No. 2024-504872 dated Jun. 9, 2026, with translation, 8 pages.

* cited by examiner

MEDIALLY STABILISING KNEE ENDOPROSTHESIS

CROSS-REFERENCE TO RELATED APPLICATIONS

This application is the United States national stage entry of International Application No. PCT/EP2022/070351, filed on Jul. 20, 2022, and claims priority to German Application No. 10 2021 119 663.9, filed on Jul. 28, 2021. The contents of International Application No. PCT/EP2022/070351 and German Application No. 10 2021 119 663.9 are incorporated by reference herein in their entireties.

FIELD

The present disclosure relates to a medially stabilizing knee endoprosthesis. Further, a corresponding inlay is proposed. The present disclosure is in the technical field of total knee arthroplasty (or "TKA" for short) or, respectively, knee total endoprosthesis (or "knee TEP" for short), which is the complete replacement of a worn or injured knee joint. The field of application of the medially stabilizing knee endoprosthesis disclosed here includes both the indication of an existent posterior cruciate ligament (Lat./engl.; or "PCL" for short) and the indication of an absent posterior cruciate ligament.

BACKGROUND

An essential objective of the present disclosure is to provide a knee endoprosthesis which allows a patient to largely perform the natural courses of movement to which he is used to, as with the previously still healthy knee. With regard to the anatomy of the knee, it is known that a femur or, respectively, thigh bone as an upper leg portion is connected to a tibia or, respectively, shin as a lower leg portion in the knee by a, in a highly simplified view, penknife-like hinge joint. Thereby, the term flexion or, respectively, knee bending generally refers to the (knee) flexion angle between a femur and a tibia when viewed in a sagittal plane or, respectively, in a sagittal section (through a respective leg).

Nowadays, the patients in the total knee arthroplasty are getting younger and younger and thus would like to be able to continue to be active in sports. However, in the state of the art, as recurring problems with known knee endoprostheses often their instability, an insufficient mobility, and pains in the anterior (or, respectively, front) region of the knee are complained about on the part of patients. The underlying causes can be of multiple origin: Firstly, an insufficient stability, especially in a range of moderate flexion, especially at a flexion angle (arc) between 20 degrees and 60 degrees (flexion), ought to be mentioned. Furthermore, insufficient movement abilities of the knee endoprosthesis at a range of deep flexion may underlie. Further, a lacking ability for mobility ideally different on the medial versus lateral side of the knee endoprosthesis may be causal.

The natural courses of movement in the healthy knee or, respectively, its natural kinematics have been studied in detail by the scientists M. A. R. Freeman and V. Pinskerova, for example, using a magnetic resonance imaging method. Hereto, reference is made to their scientific publication "The movement of the knee studied by magnetic resonance imaging" [Clin. Orthop. Relat. Res. 2003; (410) 35-43], which is hereby expressly made a part of the present disclosure document by reference. Especially, therein is found a schematic illustration of the medial and lateral contact site on the tibia during flexion in the natural knee joint (see FIG. 12). Accordingly, natural knee activities occur primarily at a flexed flexion angle between 10 degrees and 120 degrees (flexion), further up to ca. 135 degrees (flexion), and in exceptions extreme flexion up to 165 degrees flexion angle. The natural articular surfaces (or, respectively, articulating surfaces) of the (paired) femur condyles (or, respectively, articular processes or articular cartilages) of the femur are circular over this flexion angle (arc) in the sagittal section; thereby rotating about their center.

The natural medial femur condyle (or, respectively, the one facing towards the center of the body) does not move in an antero-posterial direction (or, respectively, anterior-posterior direction). Accordingly, an offset towards posteriorly, orthopedically termed as so-called "roll-back," does not occur medially in the natural knee. The natural lateral femur condyle (or, respectively, lateral one, facing away from the center of the body) tends to "roll-back," which, in the natural kinematics, triggers an internal tibial rotation with flexion. In a natural situation with a non-flexed leg, corresponding to an essentially stretched flexion angle (arc) between 0 degrees (i.e., full extension) up to 10 degrees to 30 degrees, the tibial rotation is coupled with flexion. The natural articular surfaces are formed medially with an anterior (or, respectively, front) femur facet or, respectively, femur bevel, which has a larger radius. Thus, this forms a joint with an upwardly inclined tibia facet or, respectively, tibia facet. Laterally, the femur condyle rolls towards anteriorly onto the anterior horn (anterior horn of the outer meniscus). A patient-dependent flexion beyond 120 degrees can be achieved actively and/or passively. Medially, the femur rolls onto the posterior horn (posterior horn of the outer meniscus). Laterally, the femur and posterior horn slip over the posterior tibia. In the healthy knee joint, at a flexed flexion angle (arc) between 30 degrees and 90 degrees (flexion), posterior translation of the interior and exterior meniscus and of the lateral femur condyle occurs. Thereby, the medial femur condyle remains largely stationary or translates slightly towards anteriorly.

In summary, this kinematics of the natural knee joint described in detail above means that during the knee movement the femur moves on the tibia much less medially than laterally. This circumstance is referred to, in professional terminology, as "medial pivot" (engl. "medial pivot"). The axis of rotation of the femur is on the medial side of the tibia.

Based on this knowledge, knee endoprostheses with a largely fixed medial pivot of the femur have recently been developed, which are known as "medial-pivot design" (medial-pivot construction). This type of movement is achieved in the state of the art by the combination of an asymmetrically formed femur bearing surface of a femur condylar pair together with an asymmetrically formed tibia bearing surface for joint forming of the joint of such knee endoprostheses. Thereby, the asymmetrically formed tibia bearing surface is usually arranged in form of a so-called "inlay" (or, respectively, insert, meniscus part) firmly at a distal tibia part or, respectively, firmly connected to it in order to function as a surface or, respectively, sliding surface for the femur bearing surface. Thus, an overall asymmetrically shaped tibia part is formed.

For example, EP 2 323 594 B1 discloses such a prosthetic knee joint which, for emulation of the natural kinematics of the knee, comprises a one-piece tibia part with an asymmetrically formed concave tibia bearing surface and a one-piece femur part with an equally asymmetrically formed condylar-shaped femur bearing surface. Thereby, the prosthetic knee joint disclosed therein is designed according to the “medial-pivot design” (medial-pivot construction), in summary, such that displacements of the asymmetric femur bearing surface towards a posterior direction in response to an increasing flexion of the knee result in a rotation of the femur part relative to the tibia part about an external axis of rotation and about flexion angle within a specified range. At the same time, a contact of the asymmetric tibia bearing surface and the asymmetric femur bearing surface is maintained.

However, there are several disadvantages with the solutions from the state of the art:

Firstly, the fixed medial pivot is not physiological for all activities.

Further, it is not taken into account that the knee requires more stability in the stretched state (i.e. flexion of 0 to a few degrees) than in the flexed state. Another disadvantage is that these designs have a ball socket or, respectively, ball-and-socket joint on the medial side, while the lateral side has a more planarly formed support. This means that the femur bearing surface is (quasi) completely congruent or, respectively, curve-conforming with the tibia bearing surface, especially the inlay. Accordingly, the femur rotates only on the medial side, as regards at least the predominant part or, respectively, portion, possibly the complete part, of the flexion or, respectively, of the flexion angle (arc). Thus, the pivot or, respectively, center of rotation remains stably in the same place for all activities or, respectively, courses of movement. Accordingly, the “medial-pivot design” (the medial-pivot construction) is to be considered as too restrictive for everyday life for the vast majority of patients, especially young ones. Besides the functional topic, there is in the medium term the risk of degradation of the gliding surface due to overloading.

A number of further disadvantages result from the fact that the asymmetrically formed femur bearing surface and the asymmetrically formed tibia bearing surface cooperate as two components of a combination and must therefore be well matched to each other or, respectively, suitably shaped, especially dimensioned, to each other.

Firstly, the medial-pivot design results in a problem with regard to a compatibility between different sizes of, on the one hand, the tibia of the patient or, respectively, of at least a correspondingly matching tibia bearing surface, especially the inlay, and, on the other hand, the femur of the patient or, respectively, of at least a correspondingly matching femur bearing surface. It is important for the surgeon to be able to optimally correspond to each individual situation of the patient or, respectively, indication for the patient. In this respect, it is more common for the femur and tibia to have different sizes in comparison in an individual patient, for example, a large femur size (scale 7) may meet a small tibia (scale 5). However, the medial-pivot design implies a high congruency or, respectively, a high degree of form fit medially between, on the one hand, the tibia bearing surface, especially the inlay, and, on the other hand, the femur bearing surface. Accordingly, on the medial side, the compatibility of the knee endoprosthesis according to the medial-pivot design is considerably limited what regards the above described situation of the patient with different sizes on the one hand of the tibia and on the other hand of the femur.

Further disadvantageously, the surgeon cannot use a standard femur part or, respectively, a standard femur bearing surface, preferably in a cruciate ligament-preserving manner, together with a medial pivot tibia part or, respectively, a medial pivot tibia bearing surface, especially a medial pivot inlay; or, vice versa, cannot use a medial pivot femur part or, respectively, a medial pivot femur bearing surface together with a standard tibia part or, respectively, with a standard tibia bearing surface, especially a standard inlay, preferably in a cruciate ligament-preserving manner. This disadvantageously has the consequence that if the surgeon wants to be able to use both concepts on a case-by-case basis, i.e. depending on the individual situation of the or, respectively, indication for the patient, he must keep both respective designs or, respectively, combinations or, respectively, pairings suitable for the patient in stock, i.e. the femur part or, respectively, the femur part together with the tibia part or, respectively, the tibia part on the one hand according to the medial-pivot design and on the other hand according to the standard design. This leads to a much larger space requirement for supplies to be kept in stock and to an increase of the storage costs for the treating surgeon or, respectively, the hospital.

Similarly, another disadvantage of the knee endoprosthesis according to the medial-pivot design can arise during the surgery or, respectively, intra-operatively. Namely, sometimes the case arises that, as soon as the knee endoprosthesis has been implanted, in the actual situation, due to the mechanical influence of ligaments, tendons, soft tissues, the required or, respectively, desired target degree of stability is not achieved, but either excessive stability or instability can be determined. Therefore, the surgeon must be able, at the opened knee, to afterwards modify either the femur part or the tibia part for achieving of the target degree of stability. For example, in the event that stability proves to be too great, the surgeon will want to take the measure to change the initially implanted medial pivot tibia bearing surface, especially the medial pivot inlay, to the standard tibia bearing surface, especially the standard inlay, or, respectively, to exchange for one. However, this would mean that in this case the asymmetrically formed medial pivot femur bearing surface would no longer be compatible, so that the surgeon would also have to additionally change the medial pivot femur part to a standard femur part or, respectively, standard femur bearing surface. Thus, the surgical procedure is extended in a negative way for both the surgeon and the patient.

SUMMARY

A medially stabilizing knee endoprosthesis for total knee arthroplasty with preservation or with dissection of the posterior cruciate ligament has (or, respectively, comprises): a femur bearing surface which is provided, for orientation towards distally, on a femur part configured for fixation to a distal end of a femur; and a tibia bearing surface which is provided, for orientation towards proximally, on a tibia part configured for fixation to a proximal end of a tibia. Especially, the tibia bearing surface may thereby be formed as a proximal surface of an inlay arranged and/or arrangeable proximally at the tibia part. The femur bearing surface thereby has a convex medial femur condylar bearing surface and a convex lateral femur condylar bearing surface. The tibia bearing surface thereby has a concave medial bearing shell and a concave lateral bearing shell and is configured for accommodation and slidable slide bearing of the femur bearing surface without a fixed medial pivot (point) of the femur bearing surface in the medial bearing shell. Thereby, according to the disclosure, the medial bearing shell and the lateral bearing shell form an asymmetric tibia bearing surface with respect to each other. Cumulatively, the medial femur condylar bearing surface and the lateral femur condylar bearing surface form a non-asymmetric or quasi-symmetric femur bearing surface with respect to each other. Thereby, the medial femur condylar bearing surface and the lateral femur condylar bearing surface coincide at least in an anterior femur condylar radius of respective anterior surface portions. Thereby, the asymmetric tibia bearing surface forms an outside circumferential proximal elevation contour. Thereby, the elevation contour has an anterior elevation contour portion with at least one anterior elevation point and a posterior elevation contour portion with at least one posterior elevation point. Thereby, the anterior elevation point is proximally elevated in relation to the posterior elevation point with respect to at least one sagittal plane. Thereby, an antero-medial elevation contour portion of the anterior elevation contour portion at the medial bearing shell forms a proximally most elevated anterior elevation point as an antero-medial apex point.

The term "non-asymmetric", according to the disclosure, refers to a (femur) bearing surface formed without asymmetry. Especially, this means a quasi-symmetric, further preferably symmetric, (femur) bearing surface. Thereby, the person skilled in the art understands that the comparison of the medial femur condylar bearing surface and the lateral femur condylar bearing surface is to be based on the central convex contact surfaces of the slidable slide bearing. In other words, the specific design of peripheral or, respectively, off-center or, respectively, decentral peripheral areas (on the) of the femur bearing surface or, respectively, around the femur bearing surface plays no role at all or at most a subordinate role in the evaluation of a degree of symmetry. Also, in the present case, the assessment is not a question of any production-related tolerance deviations.

In general, the skilled person understands that asymmetry in the comparison between a medial bearing surface or, respectively, bearing shell and a lateral bearing surface or, respectively, bearing shell refers to different designs with significant deviations with respect to the respective (curvature) radii and/or the guiding lines with respect to a kinematic course of movement.

In other words, the term "symmetric" ought not be construed in an absolute or sophistical sense, but with technical judgement or, respectively, with a view to the function of the slide bearing and the effect especially on the kinematics. Accordingly, the overall appearance of the femur condylar bearing surfaces in comparison of the lateral to the medial side must be considered. By the term "non-asymmetric", also preferred embodiments with minor deviations of the (curvature) radii and/or the guiding lines are comprised. In the comparison of the medial femur condylar bearing surface and the lateral femur condylar bearing surface, the term "non-asymmetric femur bearing surface" is intended to include such a preferred embodiment in that only slight deviations in the (curvature) radii serve for emulation or, respectively, consideration of the natural or, respectively, anatomical differences in both femur condyles (inner side versus outer side) in the patient.

Especially, however, the feature "non-asymmetric femur bearing surface" is intended to exclude a previously known design of a medially (highly) stable knee endoprosthesis with a fixed medial pivot of the femur, which is known as a "medial-pivot design" (medial-pivot construction). As described by way of introduction, the latter design relates to the combination of an asymmetrically formed femur bearing surface of a femur condylar pair with an asymmetric tibia bearing surface. Especially, in distinction to the state of the art, such a previously known embodiment with an asymmetrically formed femur bearing surface for forming of a medial ball-and-socket joint as slide bearing of the (spherical) medial femur condyle bearing surface on a (spherical) medial bearing shell of a tibia bearing surface does not fall under the afore-said feature of the "non-asymmetric femur bearing surface".

The asymmetric design of the tibia bearing surface of the knee endoprosthesis according to the disclosure firstly results in the advantage of a desirable medial stabilization on the medial side due to a, in comparison to a symmetric tibia-side sliding surface, higher, thus improved, congruency or, respectively, form fit of the femur bearing surface to the tibia bearing surface. Especially, the knee endoprosthesis according to the disclosure allows an optimum of a medially increased congruency, which improves the stability of the course of movement in the artificial knee joint, with at the same time laterally high kinematic degrees of freedom, which altogether supports more active and even sporting courses of movement. In summary, this results, for many indications or, respectively, for a large group of patients, in, according to all criteria, largely optimal overall kinematics and improved mobility.

The solution according to the disclosure and the technical advantages derived therefrom result from the interaction of the tibia bearing surface and the femur bearing surface in the particular combination of their respective specific shape designs for forming of the slidable slide bearing. The technical solution idea underlying the present disclosure is based on the combination of a non-asymmetric, preferably an essentially symmetric, femur bearing surface with an asymmetric tibia bearing surface, configured to form the slidable slide bearing, for the purpose of the courses of movement of an (artificial) knee joint.

Thus, is not further significant in which specific manner the tibia bearing surface is provided at the tibia part for orientation towards proximally, or, respectively, is connected to the tibia part, or, respectively, is (integrally) formed in the tibia part. Accordingly, in the ghist of the present disclosure, aspects regarding the arrangement of the tibia bearing surface at the tibia part may remain less considered. Preferably, the knee endoprosthesis may be designed in the design having a fixed support of the tibia bearing surface. Alternatively preferably, the knee endoprosthesis may be designed in the design having a movable support of the tibia bearing surface.

Thus, on the one hand, an embodiment in which the tibia bearing surface is formed as a proximal (upper) surface of the tibia part or, respectively, in the tibia part may be preferred.

On the other hand, such an embodiment may be just preferred in which the tibia bearing surface is formed as a proximal (upper) surface in a separately molded inlay (or, respectively, a meniscus-like knee prosthesis part, preferably made of a thermoplastic plastic or, respectively, a duroplast, such as for example polyethylene). That is, in this preferred embodiment based on a separate inlay, this provides a sliding surface of polyethylene between the femur part and the tibia part (or, respectively, between the femur and tibia parts) of the knee endoprosthesis. This preferred embodiment offers the advantage that the inlay serving as sliding surface for the artificial knee joint replaces the natural joint space with the menisci.

Variants of the design with regard to an arrangement of the inlay at the tibia part are equally conceivable, preferably that the inlay is floatingly supported at the tibia part, movably connected or, respectively, usable or connected or, respectively, usable in a fixed manner, for example screwed on, press-fitted, and the like.

Especially, a first-mentioned advantage of the present disclosure arises from considerations of the kinematics of the knee endoprosthesis according to the disclosure. Thus, by means of the knee endoprosthesis according to the disclosure, it is possible to emulate the natural kinematics of the healthy knee described by way of introduction to the greatest possible extent. Thereby, the natural kinematic is characterized especially by an asymmetric movement between the medial side and the lateral side of the knee. According to the disclosure, in the case of a stretched or, respectively, only slightly flexed knee, corresponding to an essentially stretched flexion angle (arc) between 0 degrees (i.e. at full extension) up to a few angular degrees, the required high stability is achieved, namely independent of the medial and lateral side. Furthermore, the knee endoprosthesis according to the disclosure maintains a still high medial stability in a range of medium flexion, especially in a flexion angle (arc) between 20 degrees and 40 degrees (flexion). Thereby, it also exhibits an advantageous antero-lateral stability. At the same time, the knee endoprosthesis according to the disclosure allows in an advantageous manner that the postero-lateral stability can decrease a little, so that the lateral femur condylar bearing surface is allowed a so-called "roll-back", i.e. an offset towards posteriorly or, respectively, a rolling-back, with simultaneous possibility for rotation. This allows significantly improved degrees of freedom in dynamic courses of movement while stability in the artificial knee joint being maintained at the same time. Finally, at high flexion, it is achieved according to the disclosure, that, for emulation of the natural kinematics, the postero-medial stability decreases only slightly and, at the same time, the postero-lateral stability is reduced largely. As a result, it is achieved that the "roll-back" on the medial side becomes low, while it can become high, related thereto, on the lateral side, while at the same time a significant rotation of the femur or, respectively, femur neck bone is enabled.

As the second-mentioned advantage with regard to the desired emulation of the natural kinematics is to be mentioned that the asymmetric design of the tibia bearing surface of the knee endoprosthesis according to the disclosure enables an advantageous dissociation of the kinematic degrees of freedom on the medial versus the lateral side.

A third-mentioned advantage relates to the point of, by means of the knee endoprosthesis according to the disclosure, a reduced complexity for the surgeon, as well as to the storage stock keeping in the clinic. Due to the fact that the medial femur condylar bearing surface and the lateral femur condylar bearing surface form a femur bearing surface being non-asymmetric, essentially symmetric, especially an axi-symmetric one with respect to a sagittal plane disposed therebetween, the femur part can be used independently of the affected knee side, i.e. for both the left knee and the right knee. This halves the number of prosthesis parts to be kept in stock on the part of the clinic or, respectively, to be differentiated in the operation, by which the complexity and the costs of the storage stock keeping or, respectively, operation planning decrease advantageously. In any case, several sizes or, respectively, thicknesses for femur parts and for tibia parts or, respectively, inlays must be kept available in a knee prosthesis product family, both on the part of the manufacturer as well as on the part of the clinic, in order to be able to respond surgically to the various patient situations. Thus, the knee endoprosthesis according to the disclosure represents a solution for the surgeon that reduces complexity and is more cost-effective.

As fourth-mentioned advantage it should be mentioned that the disclosure delivers an advantageous compatibility with respect to the knee endoprosthesis family over the size range required on the integration side. Due to the variability of the anatomy, different sizes of tibia part (or, respectively, tibia bearing surfaces) must work with different femur parts (or, respectively, femur bearing surfaces). The required compatibility over the range of sizes required by the indication presents an enormous technical challenge. As described by way of introduction, the required compatibility is especially problematic in the case of the previously known designs with a single radius for forming a (medial) ball-and-socket joint. In this respect, the problem is even amplified in the case of this prior art with a single radius, insofar as the compatibility of the sizes is quite considerably limited due to the structurally high congruency between the femur bearing surface to the tibia bearing surface on the medial side. Here, the knee endoprosthesis according to the disclosure, especially preferred embodiment described above, provides a technically advantageous solution. In this respect, there is no such restriction due to the femur condylar bearing surfaces symmetric to each other, which may each be formed with plural radii per size indication. In this way, increased bone loss is avoided according to the disclosure, since the anchoring constructions can be designed with smaller radii to fit smaller size indications.

As fifth-mentioned advantage, it should be mentioned that the present disclosure enables an implantation of the knee endoprosthesis according to the disclosure or, respectively, a total knee arthroplasty both with preservation and with dissection of the posterior cruciate ligament. Thus, a broad indication scope and a flexible approach to different indications are made possible for the surgeon. A first indication relates to a constellation in the patient in which the medial and lateral ligament, and possibly also the posterior cruciate ligament, are sufficiently stable so that the ligaments ideally to be preserved can continuously coordinate the movements of the knee, i.e. bending (flexion), stretching (extension) and turning (rotation), after successful implantation of the knee endoprosthesis according to the disclosure. A further indication relates to a constellation in the patient in which the surgeon removes the posterior cruciate ligament, possibly damaged by osteoarthritis, during the operation before the installation of the knee endoprosthesis according to the disclosure.

In addition, two further-mentioned advantages according to the disclosure result, as described below:

According to the disclosure, the asymmetric tibia bearing surface of the knee endoprosthesis defines or, respectively, forms an outside circumferential proximal elevation contour. Thereby, the elevation contour has an anterior elevation contour portion which has at least one anterior elevation point or, respectively, on which a plurality of anterior elevation points are located. The elevation contour further has a posterior elevation contour portion which has at least one posterior elevation point or, respectively, on which a plurality of posterior elevation points are located. Thereby, the anterior elevation point is proximally elevated in relation to the posterior elevation point, with respect to at least one sagittal plane or, respectively, when projected onto a sagittal plane. Preferably, the anterior elevation contour portion may be proximally elevated, especially completely, in relation to the posterior elevation contour portion. Because the entire anterior elevation contour portion is proximally (or, respectively, in the case of a patient standing upright: upwardly) elevated in relation to the entire posterior elevation contour portion, the anterior elevation contour portion is freely visible from a rear view of the tibia part, especially of the inlay. This serves especially to an advantageously further improved anterior stabilization.

Further according to the disclosure, an antero-medial elevation contour portion of the anterior elevation contour portion at the medial bearing shell forms a proximally most elevated anterior elevation point as an antero-medial apex point. In other words, the tibia bearing surface is thereby designed on the part of its height profile (oriented towards proximally) such that on the anterior side an (envelope) surface portion of the medial bearing shell is especially raised (or, respectively, elevated towards proximally) so that at least this culminates in a (proximally) highest anterior elevation point as an antero-medial apex point or, respectively, rises to such one. Accordingly, the medial femur condylar bearing surface is (slidingly) supportedly surrounded by the corresponding medial bearing shell of the tibia bearing surface, especially on the anterior side of the knee endoprosthesis, thus guided or, respectively, stabilized in the course of movement. The advantages mentioned above with respect to the kinematics are reinforced as a result.

Overall, the combination, according to the disclosure, of an, for medial stabilization, asymmetrically formed tibia bearing surface of a tibia part, especially an inlay, together with a (quasi-) symmetric femur bearing surface with femur condylar bearing surfaces (essentially) identically formed on both sides offers a good balance in the achievement of various individual, in part counter-balancing, technical objectives. Especially, on the one hand, the essential technical goal of a true-to-nature kinematic behavior or, respectively, course of movement, even for patients with high kinematic requirement in terms of stability and “range of motion” (i.e. range of movement for e.g. sports, Asian lifestyle), is served after implantation of the knee endoprosthesis according to the disclosure taken place or, respectively, a total knee arthroplasty. And on the other hand, the further technical goal of an increased efficiency and reduced complexity for the surgeon or, respectively, the clinical procedure is also according to the disclosure considerably supported.

Insofar as the present disclosure relates to a technical solution without a fixed medial pivot point of the femur bearing surface in the medial bearing shell, it overcomes the fundamental disadvantages described by way of introduction to the state of the art in the field of the “medial-pivot design” (the medial-pivot construction).

Presently, the terms used for the anatomical designation of position and direction are used as specialist or, respectively, anatomical terms. Thus, the position and direction designations proximal [lat. proximus “nearest”; (arranged or, respectively, aligned) towards the body center (of the patient, not of the surgeon)]; in contrast to distal [lat. distare “to be distant”; away from the body center (of the patient)] are used.

Further, presently with reference to a knee joint or, respectively, the knee endoprosthesis, the position and direction designation medial [lat. medium “center”; towards the median plane] means inside or, respectively, on the inside of the knee (arranged or, respectively, aligned towards it). In contrast thereto, the position and direction designation lateral [lat. latus “side”; away from the median plane, towards the side] means outside, on the outside of the knee (arranged or, respectively, aligned towards it).

The position and direction designation anterior [Latin ante “in front of”] means front(al), lying in front, which presently corresponds to ventral [towards the front side, concerning the abdomen]. In the natural knee, the knee cap [lat. patella] thus lies anteriorly. In contrast thereto, the position and direction designation posterior [Latin post “behind”] means rear, lying behind, which presently corresponds to dorsal [located at the or, respectively, towards the back].

The three mutually orthogonal anatomical spatial axes or, respectively, directions are designated as follows: The longitudinal axis extends in a height direction [top side, above↔bottom side, below], especially in the patient standing upright vertically from the crown of the head to the sole of the foot, here preferably through the knee. Further, the sagittal axis [lat. sagitta “arrow”; anterior, front↔posterior, rear] runs in a depth direction, esp. in front view of the patient standing upright. Further, the transversal axis [medial, inside↔lateral, outside, e.g. right↔left] extends in a width direction, especially in front view of the patient standing upright.

The anatomical term frontal plane refers to a plane perpendicular or, respectively, orthogonal to a sagittal plane and a transverse plane. Thereby, the sagittal plane refers especially to a plane that divides the femur or, respectively, tibia into a right and a left (knee) half. The transverse plane is a plane (horizontal in a patient standing upright) that is perpendicular to a longitudinal axis, especially one of the tibia.

A condylar-shaped surface refers to a (surface) area located at a distal end of a femur part that mimics the shape of an anatomical or, respectively, natural femur condyle.

The specialist term of the (curve) conformity (or, respectively, conform) between two curves or, respectively, according to the disclosure between (respective adjacent curve sections) of a tibia bearing surface and a femur bearing surface (when projected onto a sectional plane, especially onto a medial and/or central and/or lateral sagittal plane) means that the corresponding radii at a contact point essentially or, respectively, nominally correspond or, respectively, are equal to each other. In this respect, the conformity relates to a measure of the bearing form fit between (respective curve sections of) the tibia bearing surface to the femur bearing surface.

On the other hand, a lack of (curve) conformity leads to a laxity as opposite term, i.e. in the sense of a high bearing clearance or, respectively, a low bearing form fit. In other words, laxity is a measure for a displacement or, respectively, an offset and/or for an (angular) rotation and/or for a kinematic degree of freedom, which can occur due to a lack of (curve) conformity between (respective adjacent curve sections) of a tibia bearing surface and a femur bearing surface.

The specialist term of the external rotation of the femur refers to the rotation of the femur about an external rotation axis, which is located at the medial bearing shell of the tibia part and is parallel to the longitudinal axis of the tibia part.

Preferably, alternatively or cumulatively, the anterior elevation point, with respect to at least one sagittal plane or, respectively, when projected onto a sagittal plane, may form or, respectively, define an anterior bearing height. Thereby, the anterior bearing height is related to a proximally lowest bearing low point in the (respectively corresponding) concave medial and/or lateral bearing shell. Thereby, the posterior elevation point forms a posterior bearing height or, respectively, defines such one, with respect to at least one sagittal plane or, respectively, when projected onto a sagittal plane. Thereby, the posterior bearing height, likewise like also the anterior bearing height, is related to the proximally lowest bearing low point in the (respectively corresponding) concave medial and/or lateral bearing shell. In this preferred embodiment, the anterior bearing height is greater than the posterior bearing height. Still further preferably, the maximum anterior bearing height is formed at the antero-medial apex point. Also in this preferred embodiment, the advantages mentioned above with respect to kinematics are further enhanced. Especially, the antero-medial stabilization is further optimized.

Preferably, alternatively or cumulatively, the medial bearing shell of the knee endoprosthesis may be shaped such that, when viewed in a medial sagittal plane, a pitch triangle is spanned from the anterior elevation point with the anterior bearing height to the proximally lowest bearing low point in the medial bearing shell. Thereby, the pitch triangle forms a medial pitch angle located at the proximally lowest bearing low point. Especially, the medial pitch angle measures 12 to 32 degrees, more preferably 17 to 27 degrees, especially ca. 22 degrees. This preferred value range or, respectively, value of the medial pitch angle offers an optimum with regard to the antero-medial stabilization in the artificial knee joint.

Preferably, alternatively or cumulatively, with respect to the femur bearing surface of the knee endoprosthesis according to the disclosure, the medial femur condylar bearing surface and the lateral femur condylar bearing surface may be formed, essentially, condylar-shaped. As a result, the shaping of the femur part is especially optimized.

Preferably, alternatively or cumulatively, a posterior (curve) portion of the medial femur condylar bearing surface and the lateral femur condylar bearing surface, respectively, may be formed in a range of 0 to 95 degrees of flexion angle (arc) with a steady or, respectively, constant posterior radius. In this preferred embodiment, the advantages mentioned above are further magnified.

Preferably, alternatively or cumulatively, a most distal (or, respectively, most distally disposed) point of the medial femur condylar bearing surface may form a medial extension bearing surface contact point which is in contact with the medial bearing shell of the tibia bearing surface when the leg is stretched or, respectively, at ca. 0 degrees of flexion angle (i.e., extension). Especially, the medial extension bearing surface contact point, when with a stretched leg or, respectively, ca. 0 degrees of flexion angle (i.e., extension) with respect to a sagittal plane as angular segment related to an anterior edge of the medial femur condylar bearing surface, may thereby be located at 50 to 70 degrees, more preferably at 58 to 62 degrees, especially at ca. 60 degrees. Alternatively or cumulatively, especially, the medial extension bearing surface contact point, when at ca. 0 degrees of flexion angle with respect to a sagittal plane as angular segment related to an anterior edge of the medial tibia bearing surface, may be located at 55 to 75 degrees, more preferably at 63 to 67 degrees, especially at ca. 65 degrees. Also in this preferred embodiment, the advantages mentioned above with respect to kinematics are further enhanced. Especially, the medial stabilization is still further optimized.

Even more preferably, the medial extension bearing surface contact point may coincide with the proximally deepest bearing low point in the concave medial and/or lateral bearing shell. All these features promote a medial stabilization.

Overall, the preceding preferred embodiments of the present disclosure result, with respect to consideration of the involute, in a more posteriorly disposed extension bearing surface contact point in an advantageously medially stabilizing manner, as well as, with respect to the medial bearing shell, in a larger anterior radius and a, by comparison, smaller posterior radius.

Preferably, alternatively or cumulatively, the concave medial bearing shell may form or, respectively, define, with respect to a medial sagittal plane, at least one anterior surface portion having a first radius which forms or, respectively, defines an antero-medial tibia bearing surface radius, and at least one posterior surface portion having a second radius different from the first radius, preferably smaller, which forms or, respectively, defines a postero-medial tibia bearing surface radius. This serves to a further optimized kinematic and mobility.

Especially, the antero-medial tibia bearing surface radius may thereby be formed congruent, especially identical, to an anterior femur condylar radius. Thereby, the anterior femur condylar radius is formed or, respectively, defined as a third radius of an anterior surface portion of the medial femur condylar bearing surface. It may be further preferred that the anterior femur condylar radius or, respectively, third radius is predetermined according to a femur size class for a patient. This serves to a further optimized kinematic, in terms of congruency and mobility. Further, this serves to an optimization of the clinical size management for a knee endoprosthesis family.

Alternatively or cumulatively, the postero-medial tibia bearing surface radius may thereby be formed congruent, especially identical, to a posterior femur condylar radius. Thereby, the posterior femur condylar radius is formed or, respectively, defined as a fourth radius of a posterior surface portion of the medial femur condylar bearing surface. It may be further preferred that the posterior femur condylar radius or, respectively, fourth radius is predetermined according to a femur size class for a patient. Accordingly, advantages are achieved with regard to a positive congruency as well as a sufficient stability required on the medial side. Further, this serves to a further optimized clinical size management for a knee endoprosthesis family.

Preferably, alternatively or cumulatively, the concave lateral bearing shell may form or, respectively, define, with respect to a lateral sagittal plane, at least one anterior surface portion having a fifth radius which forms or, respectively, defines an antero-lateral tibia bearing surface radius, and at least one posterior surface portion having a sixth radius different from the fifth radius, preferably larger, which forms or, respectively, defines a postero-lateral tibia bearing surface radius. This can also have a positive kinematic effect.

Especially, the antero-lateral tibia bearing surface radius or, respectively, fifth radius may be formed congruent, especially identical, to the (above defined) anterior femur condylar radius or, respectively, third radius.

Alternatively or cumulatively, the postero-lateral tibia bearing surface radius or, respectively, sixth radius thereby may especially be larger than the (above defined) posterior femur condylar radius or, respectively, fourth radius. Thereby, it may be further preferred that the postero-lateral tibia bearing surface radius is sized at least 110 percent larger than the posterior femur condylar radius. Especially, the postero-lateral tibia bearing surface radius is equal to or greater than a radius measuring 80 mm.

From the preferred matching of the, especially medial, posterior tibia bearing surface radius to the size of the posterior femur condylar radius results a more elevated (towards proximally) posterior elevation contour portion (or, respectively, a high posterior lip). This does indeed serve to a good stability, especially for the medial side. However, the patients require a high degree of flexion for some (more athletic) activities involving deep bendings of the knee. Thus it is required that femoral roll-back (somewhat medial and esp. lateral) and rotation occur. With a high posterior lip, the bone and the inlay can come into conflict with high flexion, esp. on the medial side, which can lead to pain and very limited movements.

For a solution to the problem described above, a postero-medial phase may be provided, alternatively or cumulatively, preferably at the medial bearing shell, extending obliquely towards distally from the posterior elevation point (defined above). This serves to substract peripheral material (from the outer envelope surface of the medial bearing shell). Thereby, the postero-medial phase, when projected in a sagittal plane, is at a posterior phase angle to a transverse plane. Especially, the postero-medial phase may be chamfered or, respectively, beveled with a posterior phase angle from 30 to 40 degrees, more preferably from 33 to 37 degrees, especially of ca. 35 degrees. Thus, a conflict between the bone and a postero-medial elevation contour portion (or, respectively, a proximal edge of the posterior lip of the medial bearing shell) is advantageously avoided, which would otherwise occur at high flexion. Especially, this feature supports the demands of patients with Asian lifestyle or, respectively, sport types with high flexion. Accordingly, while maintaining of the good stability, bone wear or pains at this postero-medial point can be avoided in advance.

Preferably, alternatively or cumulatively, a postero-lateral phase extending obliquely towards distally at the posterior elevation point may be provided at the lateral bearing shell. Comparable to the postero-medial phase, this serves to substract (from the outer envelope surface of the lateral bearing shell) peripheral material. Thereby, the postero-lateral phase, when projected in a sagittal plane, is at a posterior phase angle to a transverse plane. Especially, the postero-lateral phase may be formed with a posterior phase angle from 5 to 15 degrees, more preferably from 8 to 12 degrees, especially of ca. 10 degrees. Alternatively or cumulatively, the postero-lateral phase may be rounded with a postero-lateral curvature radius from 10 to 14 mm, more preferably from 11.2 to 12.8 mm, especially of ca. 12 mm. This measure also advantageously prevents bone wear and pains.

Preferably, alternatively or cumulatively, the tibia bearing surface may form an anterior patella bulge or, respectively, patella (tendon) cutout, provided centrally between the medial bearing shell and the lateral bearing shell, with a (essentially) concave outer body contour. Especially, the patella bulge may be formed congruent to a patella (tendon) size class predetermined for a patient. Alternatively or cumulatively, the patella bulge may correspond to a statistically-anthropometrically predetermined 50-percentile value for a patella (tendon) size distribution with respect to a representative, especially region-specific, population. This serves to provide an improved range of movement for performing its anatomical or, respectively, kinematic function to the patella (tendon).

Especially, the patella bulge may be formed asymmetrically. This serves to enable the formation of a proximally more elevated elevation contour portion at the medial bearing shell than at the lateral bearing shell. In this respect, the patella bulge is formed asymmetrically in order to form, in the central area of the tibia bearing shell, a steeper rise of the anterior elevation contour portion towards the antero-medial apex point.

Preferably, alternatively or cumulatively, the medial femur condylar bearing surface and the lateral femur condylar bearing surface may form a femur bearing surface that is, essentially, axisymmetric with respect to a sagittal plane disposed therebetween. This serves all five groups of advantages mentioned in detail above.

Preferably, alternatively or cumulatively, the medial femur condylar bearing surface may have, at least in a distal-medial surface portion, a medial femur condylar bearing surface radius, especially for emulating a natural medial femur condylar radius, remaining constant (or, respectively, in a constant manner). Thereby, the lateral femur condylar bearing surface has, at least in a lateral-medial surface portion, another lateral femur condylar bearing surface radius, especially for emulating a natural lateral femur condylar radius, remaing constant (or, respectively, in a constant manner). Thereby, the medial femur condylar bearing surface radius and the lateral femur condylar bearing surface radius may differ slightly from each other, namely maximally by a ratio factor from 0.8 to 1.2, preferably from 0.9 to 1.1, especially from 0.95 to 1.05. Thus, an even further improved adaptation to the anatomical situation of a patient in light of the disclosure is possible.

Preferably, alternatively or cumulatively, the tibia bearing surface may be configured for accommodation and slidable slide bearing of the femur bearing surface along a guiding curvature line formed by a plurality of contact points, so that during a flexing bending of the knee endoprosthesis from 30 degrees to ca. 90° degrees of flexion angle, a specific course of movement [in real life (e.g. in the articulator before an operation and/or after implantation in the patient) and/or virtually (e.g. simulatable in the computer model using the 3D finite element method)] is triggered or, respectively, evolved or, respectively, is caused, as quantifiable based on the following (alternative and especially cumulative) kinematic (sub)criteria:

(i) Further, an external rotation of the femur part about an external rotation axis parallel to a longitudinal axis of the tibia part, which is arranged especially at the medial bearing shell, is thereby preferably effected.

(ii) Further, a femoral roll-back is preferably thereby effected. Further preferably, the femoral roll-back may be less than or equal to minus 1.5 mm at 30 degrees and/or less than or equal to minus 6 mm at 60 degrees and/or less than or equal to minus 11 mm at a flexion angle of ca. 90 degrees [in this respect, values in the negative range if related to the roll-front axis, i.e. to a coordinate axis positive in forward direction]. Accordingly, this means that preferably an amount value of the femoral roll-back may be greater than or equal to 1.5 mm at 30 degrees and/or greater than or equal to 6 mm at 60 degrees and/or greater than or equal to 11 mm at ca. 90 degrees flexion angle.

(iii) Further preferably, the femur movement may change from a (anyway minimal) roll-front to the roll-back (further increasing in amount) in a reversal range at ca. 10 to 20 degrees, esp. ca. 14 degrees, flexion angle.

(iv) Further preferably, (until the reversal range is reached) at ca. 10 to 20 degrees, esp. ca. 14 degrees, flexion angle (i.e., in the low or, respectively, early flexion), the femur roll-front may be less than or equal to 2 mm, esp. less than or equal to ca. 0.5 mm.

All of the above-mentioned alternative or cumulative, independent, features can contribute concretely to further optimization of the kinematic. Especially, depending on the individual case of the patient or, respectively, a patient group with specific anamneses, diagnoses, needs, etc., a single (sub)feature or several or, respectively, all (sub)features in combination or, respectively, synergistically may or may just not be preferred.

Preferably, alternatively or cumulatively, the tibia bearing surface may be configured for accommodation and slidable slide bearing of the femur bearing surface, so that during a flexing bending of the knee endoprosthesis from 30 degrees to ca. 90 degrees of flexion angle, a specific course of movement [in real life and/or virtually (e.g., simulatable in a computer model)] is effected, as quantifiable based on the following (alternative and especially cumulative) kinematic (sub)criteria:

- a medial posterior movement by delta 1 mm to 4 mm is caused; and/or;
- a lateral posterior movement by delta 8 mm to 11 mm is caused.

This advantageously results in a stable stance leg phase and free swing phase.

As a second aspect of the present disclosure, a corresponding inlay configured for a knee endoprosthesis according to the disclosure is proposed. Thereby, as already explained above, the inlay is proximally arranged at the tibia part of the knee endoprosthesis, especially integrally formed with the tibia part, and/or arrangeable. Thereby, a proximal surface of the inlay forms the tibia bearing surface having a concave medial bearing shell and a concave lateral bearing shell. The tibia bearing surface is configured for accommodation and slidable slide bearing of the femur bearing surface having a convex medial femur condylar bearing surface and a convex lateral femur condylar bearing surface without a fixed medial pivot of the femur bearing surface in the medial bearing shell. Thereby, the medial bearing shell and the lateral bearing shell form an asymmetric tibia bearing surface with respect to each other; and the medial femur condylar bearing surface and the lateral femur condylar bearing surface form a non-asymmetric femur bearing surface with respect to each other. Especially, the non-asymmetric femur bearing surface may be formed as an axisymmetric femur bearing surface with respect to a sagittal plane disposed or, respectively, central between the medial femur condylar bearing surface and the lateral femur condylar bearing surface. Thereby, the medial femur condylar bearing surface and the lateral femur condylar bearing surface coincide at least in an anterior femur condylar radius of respective anterior surface portions. Thereby, the asymmetric tibia bearing surface forms an outside circumferential proximal elevation contour. Thereby, the elevation contour has an anterior elevation contour portion with at least one anterior elevation point and a posterior elevation contour portion with at least one posterior elevation point. Thereby, the anterior elevation point is proximally elevated in relation to the posterior elevation point with respect to at least one sagittal plane. Thereby, an antero-medial elevation contour portion of the anterior elevation contour portion at the medial bearing shell forms a proximally most elevated anterior elevation point as an antero-medial apex point.

This offers advantages especially with regard to a separate production (e.g. non-metal processing, injection molding, etc.) of the inlay configured for the knee endoprosthesis according to the disclosure as such and with regard to its logistical material flow in and out of the factory or, respectively, in the clinical processes.

In the following, advantageous embodiments of the present disclosure are explained in more detail with reference to the accompanying figures.

DETAILED DESCRIPTION

Figure 1:
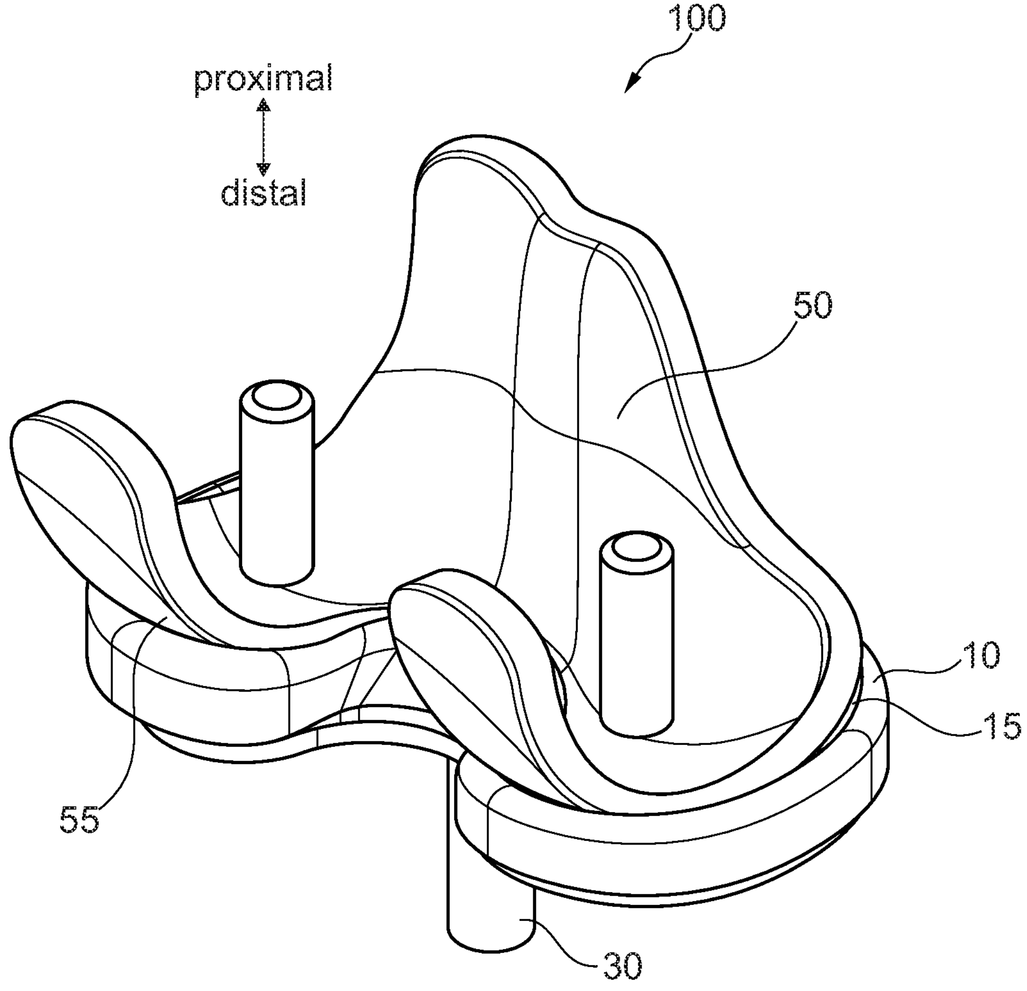
FIG. 1 is a perspective schematic illustration of a knee endoprosthesis for a total knee arthroplasty, viewed from a postero-lateral viewpoint, especially illustrating an entire arrangement with a femur part configured for distal fixation to a femur, having a femur bearing surface, and a tibia part configured for proximal fixation to a tibia, having a tibia bearing surface, arranged below or, respectively, distal thereto.
Figure 9:
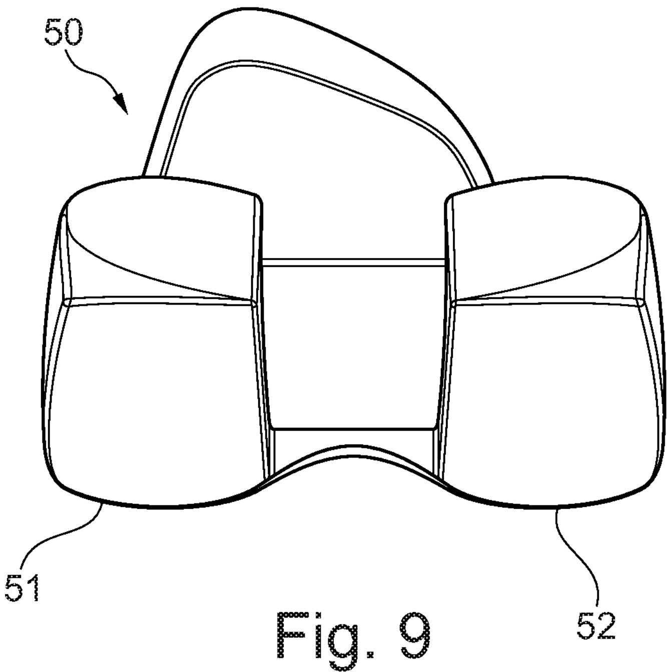
FIG. 9 is a first (slightly) perspective view of a femur part according to the embodiment of the knee endoprosthesis according to the present disclosure, viewed from a posterior viewpoint, especially for illustration of a femur bearing surface, symmetrically formed with a medial femur condylar bearing surface and a lateral femur condylar bearing surface.
Figure 10:
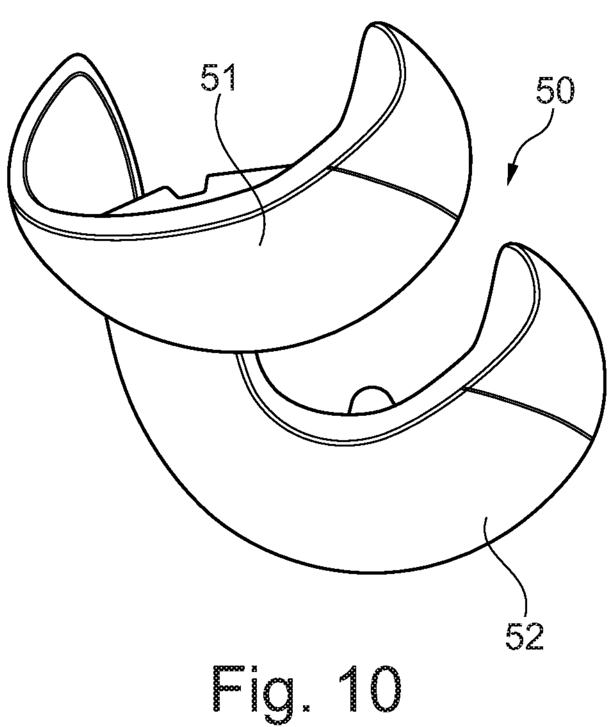
FIG. 10 is a second perspective view of a femur part according to the embodiment, viewed from an obliquely distal viewpoint, in a viewing direction onto the femur bearing surface oriented towards distally (or, respectively, against the underside of the femur part)

FIG. 1 shows a perspective schematic view of a knee endoprosthesis 100 according to the disclosure for illustration of an overall arrangement for a total knee arthroplasty, as viewed from a postero-lateral viewpoint:

A femur part 50 (or, respectively, the upper thigh or femur component) as a proximal (upper) part of the knee endoprosthesis 100 according to the disclosure may preferably be provided with two condylar half-shells for forming a femur bearing surface. With reference to the FIGS. 9 and 10 illustrating the femur part 50 taken by itself, it may be anticipated here that the femur bearing surface has a convex medial femur condylar bearing surface 51 and a convex lateral femur condylar bearing surface 52. Thereby, the lateral femur condylar bearing surface 52 is formed (essentially) the same as or, respectively, symmetric to the medial femur condylar bearing surface 51.

As schematically indicated in FIG. 1, the femur part 100 is configured to be placed by a surgeon at the distal end of the femur (at the condyles or, respectively, articular cartilages) after removal of the damaged articular surfaces. For example, the femur part 100 may be anchored towards proximally in the femur bone with the two joint pins (vertically raised in the illustration of FIG. 1), shown only by way of example.

FIG. 1 also illustrates the anchoring of the knee endoprosthesis 100 on the distal side (in the illustration of FIG. 1: on the bottom side) of a tibia part 10 mounting the femur part in a slidingly displaceable manner or, respectively, in a slidingly bearing manner. Thus, at the tibia part 10 there is a short shaft 30, illustrated only by way of example, which can be anchored in the lower leg bone towards distally. Preferably, the shaft 30 or, respectively, the distal anchoring structure of the tibia part 10 may be made of a metal alloy and/or ceramic and/or of a, preferably thermoplastic and/or duroplastic, polymer, for example, of polyethylene ("all-poly" tibia) and/or high-performance polymer (e.g.: PEEK).

The tibia part 10 (or, respectively, the shin bone, lower leg or tibia part) as a distal (lower) part of the knee endoprosthesis 100 according to the disclosure may preferably be formed in the manner of a flat disc or, respectively, plateau-shaped support structure. The tibia part 10 is provided in the sense of a counter-bearing component to the femur part 10 to replace, as a tibia bearing surface, an articular surface of a natural tibia.

Especially, (with reference to the following FIGS. 2 to 8) the tibia bearing surface 11 may be formed as a proximal surface of an inlay 20 proximally arranged and/or arrangeable at the tibia part 10. This will be described in detail in the following with reference to the related illustrations for the inlay 20 according to a preferred embodiment of the present disclosure.

Figure 2:
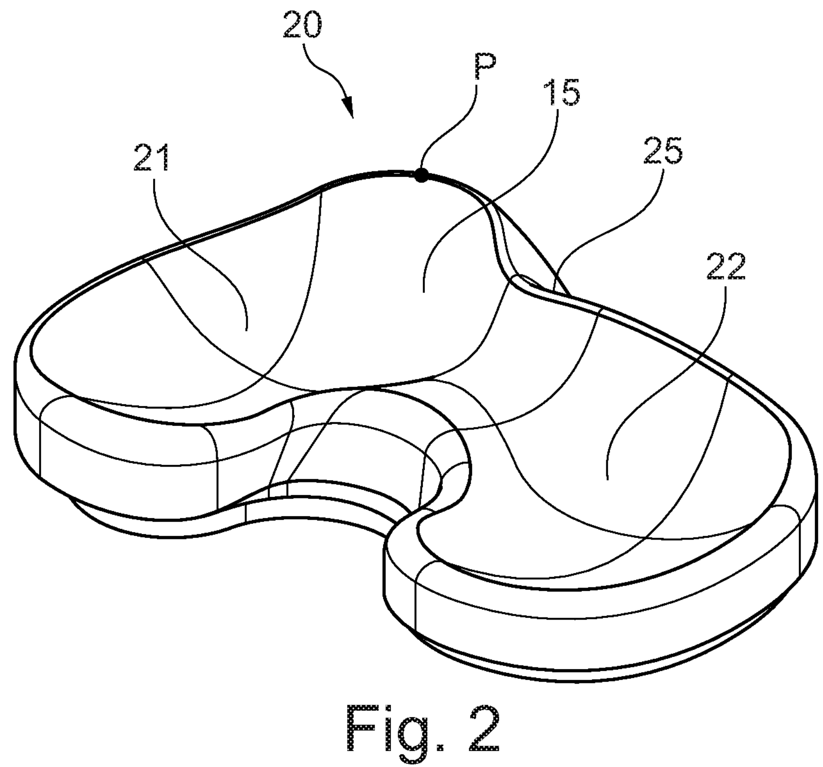
FIG. 2 is a perspective top view of an inlay of a medially stabilizing knee endoprosthesis according to a preferred embodiment according to the present disclosure, viewed from a postero-lateral viewpoint, in a viewing direction onto the inlay as the tibia bearing surface oriented towards proximally (or, respectively, onto the upper surface of the tibia or, respectively, of the tibia part), especially for illustration of a medial bearing shell and a lateral bearing shell.
Figure 3:
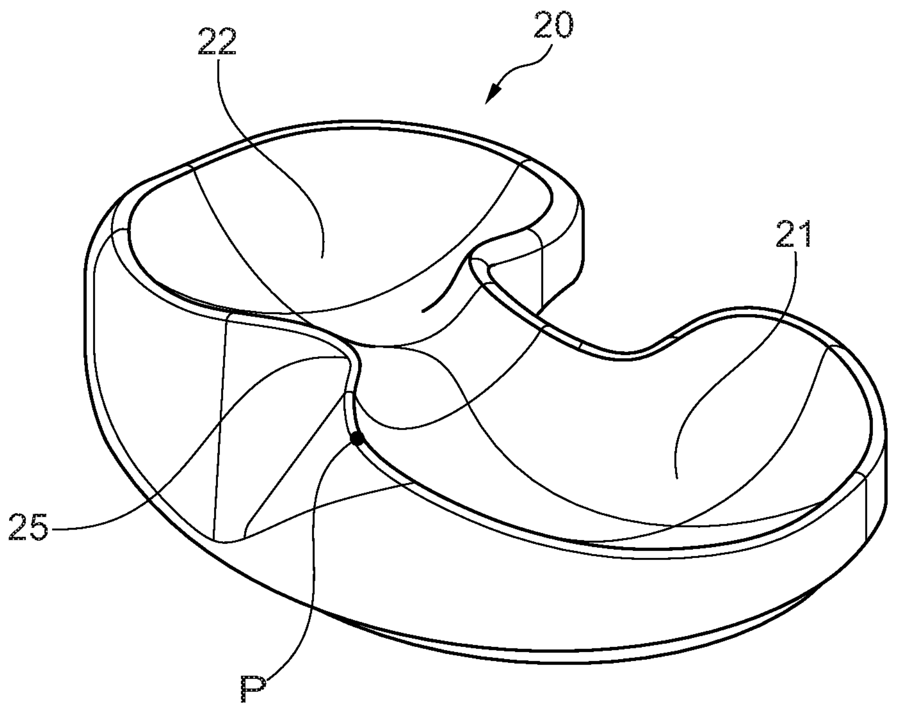
FIG. 3 is a perspective view (rotated about 180° in space relative to the top view of FIG. 2) of the inlay of the knee endoprosthesis according to the embodiment, viewed from an antero-medial viewpoint.
Figure 4:
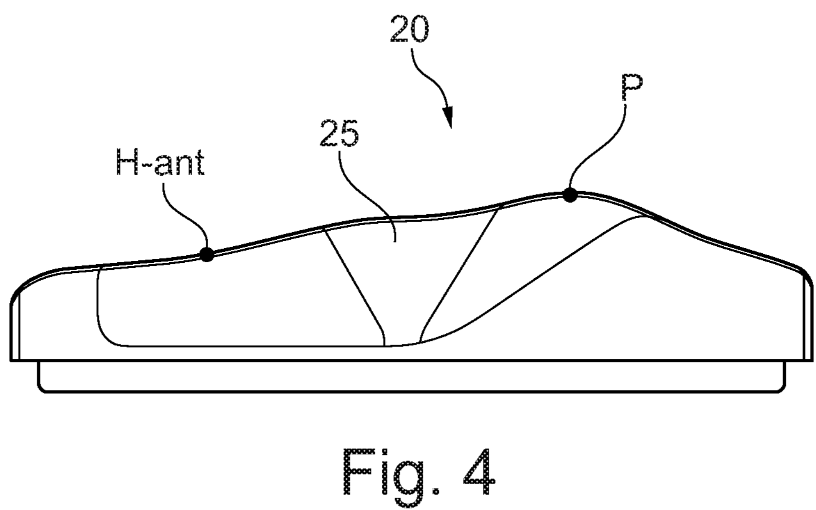
FIG. 4 is an anterior view of the inlay of the knee endoprosthesis according to the embodiment.

FIGS. 2 to 8 show different views of the inlay 20 of the medially stabilizing knee endoprosthesis 100 according to the embodiment according to the present disclosure. Thus, FIGS. 2 and 3 show perspective views, viewed from a postero-lateral viewpoint (FIG. 2) or, respectively, from an antero-medial viewpoint (FIG. 3). In a viewing direction onto a tibia bearing surface 11 oriented towards proximally (i.e., with a patient standing upright: onto the upper side of the tibia or, respectively, of the tibia part 10 of FIG. 1), an, essentially concave, medial bearing shell 21 and an, essentially concave, lateral bearing shell 22 can be seen therein. The respectively corresponding convex medial femur condylar bearing surface 51 and convex lateral femur condylar bearing surface 52 (cf. FIGS. 9 and 10) can be slidably slide-bearing-supported on these. Thereby, the medial bearing shell 21 and the lateral bearing shell 22 are arranged side by side, along a transverse axis.

Figure 5:
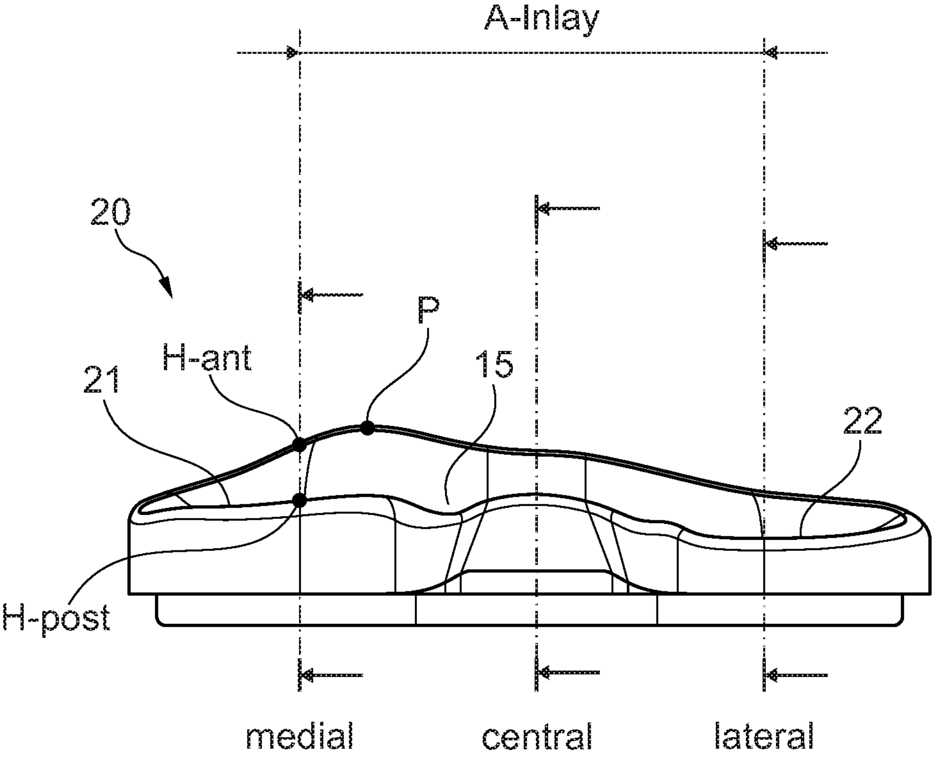
FIG. 5 is a posterior view (rotated about 180° in space relative to the view of FIG. 4) of the inlay of the knee endoprosthesis according to the embodiment, especially for illustration of the respective position of a medial cross-section, of a central cross-section as well as of a lateral cross-section (especially essentially in a sagittal plane)

The medial bearing shell 21, which defines a medial region of the tibia bearing surface 15, and the lateral bearing shell 22, which defines a lateral region of the tibia bearing surface 15, enclose between them a central region of the tibia bearing surface 15 (cf. in FIG. 5 the designation of a medial, central or lateral sagittal sectional plane, respectively). Thereby, the tibia bearing surface 15 is narrowed in the central region. Further, the tibia bearing surface is shaped in a slight U-shape or, respectively, in kidney dish shape, with the opening of the shape facing towards posteriorly.

The central region transitions anteriorly into a bulge or, respectively, a cutout, a curvature, which serves as an anterior patella bulge 25 (FIGS. 2, 3 and 6) to create space for the spatial movement of a patella (tendon). For this purpose, a (proximal) elevation contour surrounding the tibia bearing surface 15 is formed antero-centrally (essentially) concave. Thereby, the patella bulge 25 corresponds to a predetermined radius of curvature of an individual and/or typical patella (tendon) with respect to the size of the concave curvature. As can be seen especially from the top view in FIG. 6, the patella bulge 25 is asymmetrically formed. This serves to allow the formation of an elevation contour portion that is proximally more raised at the medial bearing shell 21 than at the lateral bearing shell 22. In this respect, the patella bulge is asymmetrically formed in order to form, in the central region of the tibia bearing shell 15, a steeper rise of the anterior elevation contour portion towards the antero-medial apex point P.

As can be further seen especially from FIGS. 2 and 3 with their perspective form of illustration, the medial bearing shell 21 and the lateral bearing shell are (three-dimensionally) shaped differently with regard to their three-dimensional envelope contour, especially with regard to their proximal elevation contour (recognizable as an outside circumferential continuously-drawn body edge). Thus, the medial bearing shell 21 is overall more pronounced towards proximally (or, respectively, upward). In this respect, the medial bearing shell 21 is raised at its anterior side or, respectively, in an antero-medial elevation contour portion of the anterior elevation contour portion for forming of an anterior lip to culminate in an antero-medial apex point P. Thereby, the antero-medial apex point P coincides with at least one point most elevated towards proximally (or, respectively, highest in relation to a transverse plane). This preferred shaping causes that the slide bearing guidance is more pronounced on the medial side than on the lateral side.

Thus, the medial bearing shell 21 and the lateral bearing shell 22 form a tibia bearing surface 15 asymmetric with respect to each other. Especially, the asymmetry is related to or, respectively, formed on a sagittal plane lying between them, i.e. central.

Figure 7:
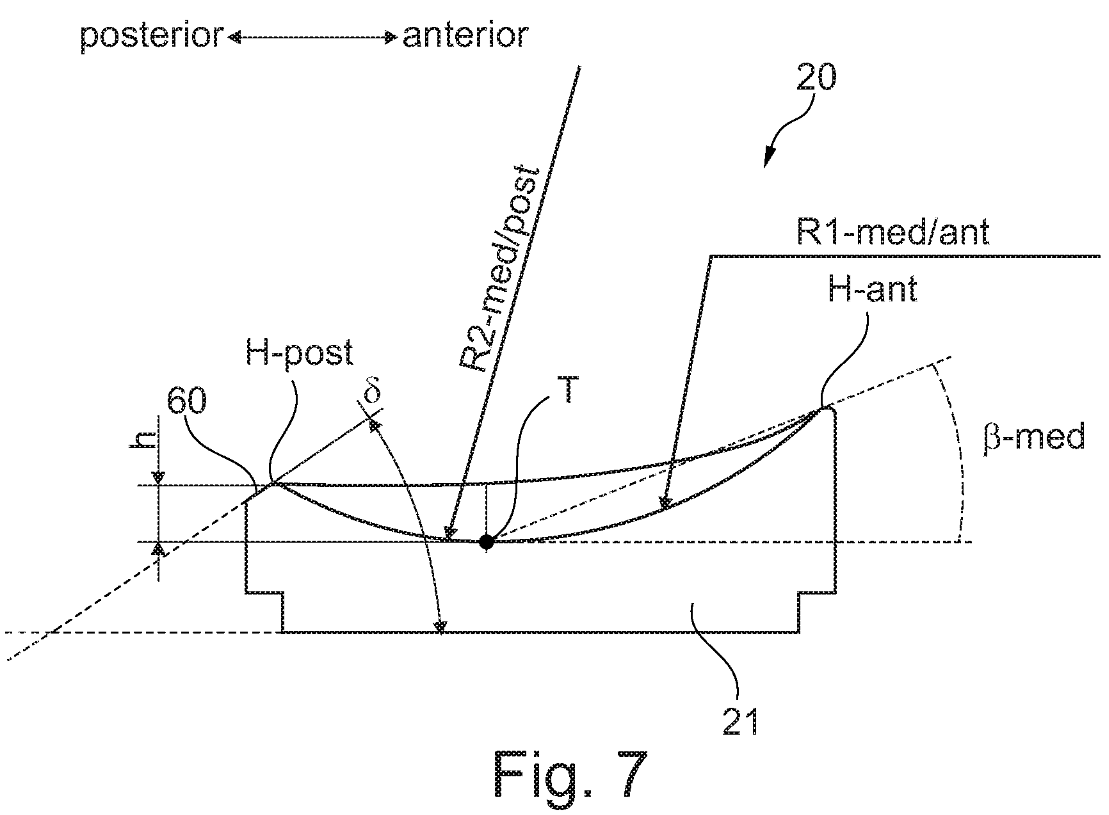
FIG. 7 is, with reference to FIG. 5, a sectional view of the medial cross-section of the inlay of the knee endoprosthesis according to the embodiment, especially for illustration of a tibia-side curvature line of the medial bearing shell in posterior-anterior direction.
Figure 11A:
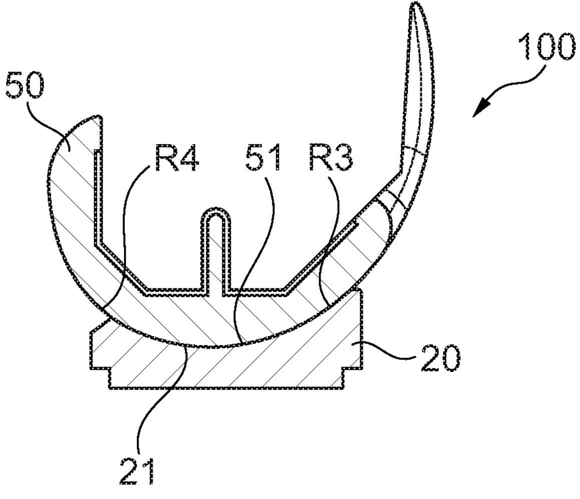
FIGS. 11*a* to 11*c* are, with reference to FIG. 5, respective sectional views of the knee endoprosthesis according to the embodiment for the medial cross-section, the central cross-section and the lateral cross-section, respectively, esp. for illustration of a congruency of the tibia-side curvature line of the inlay to a femur-side curvature line of the femur part, along the posterior-anterior direction, in a stretched knee endoprosthesis (i.e., at a flexion angle of ca. zero angular degrees)

As can be seen especially from the reference signs in FIG. 5, showing a rear view (from posterior) of the inlay 20, shows the proximal elevation contour surrounding on the outside the asymmetric tibia bearing surface 15 with the medial bearing shell 21 and the lateral bearing shell 22. On an anterior elevation contour portion of the elevation contour (rear contour line in FIG. 5) lies a plurality of anterior elevation points H-ant. On a posterior elevation contour portion of the elevation contour (front contour line in FIG. 5) lies a plurality of posterior elevation points H-post. As shown in FIG. 5, all anterior elevation points H-ant are proximally elevated or, respectively, higher in relation to all posterior elevation points H-post. Especially, this is true for the medial and central and lateral sagittal planes, which are indicated by dash-dotted lines as the respective sectional planes. The corresponding cross-sectional views are shown in the views of FIGS. 7 and 11*a* (medial section); of the FIG. 11*b* (central section); and of the FIGS. 8 and 11*c* (lateral section). In other words, the entire anterior elevation contour portion is elevated (towards) proximally in relation to the entire posterior elevation contour portion. In other words, the entire posterior elevation contour portion is lowered (towards) distally in relation to the entire anterior elevation contour portion. This is also reflected in the fact that, in the front view of the inlay 20 of the knee endoprosthesis 100 according to the embodiment shown in FIG. 4, the view onto the entire posterior elevation contour portion remains hidden behind the anterior elevation contour portion. Thereby, the antero-medial apex point P forms the at least one proximally most elevated (or, respectively, highest in relation to a transverse plane) elevation point H-ant on the anterior elevation contour portion.

Figure 6:
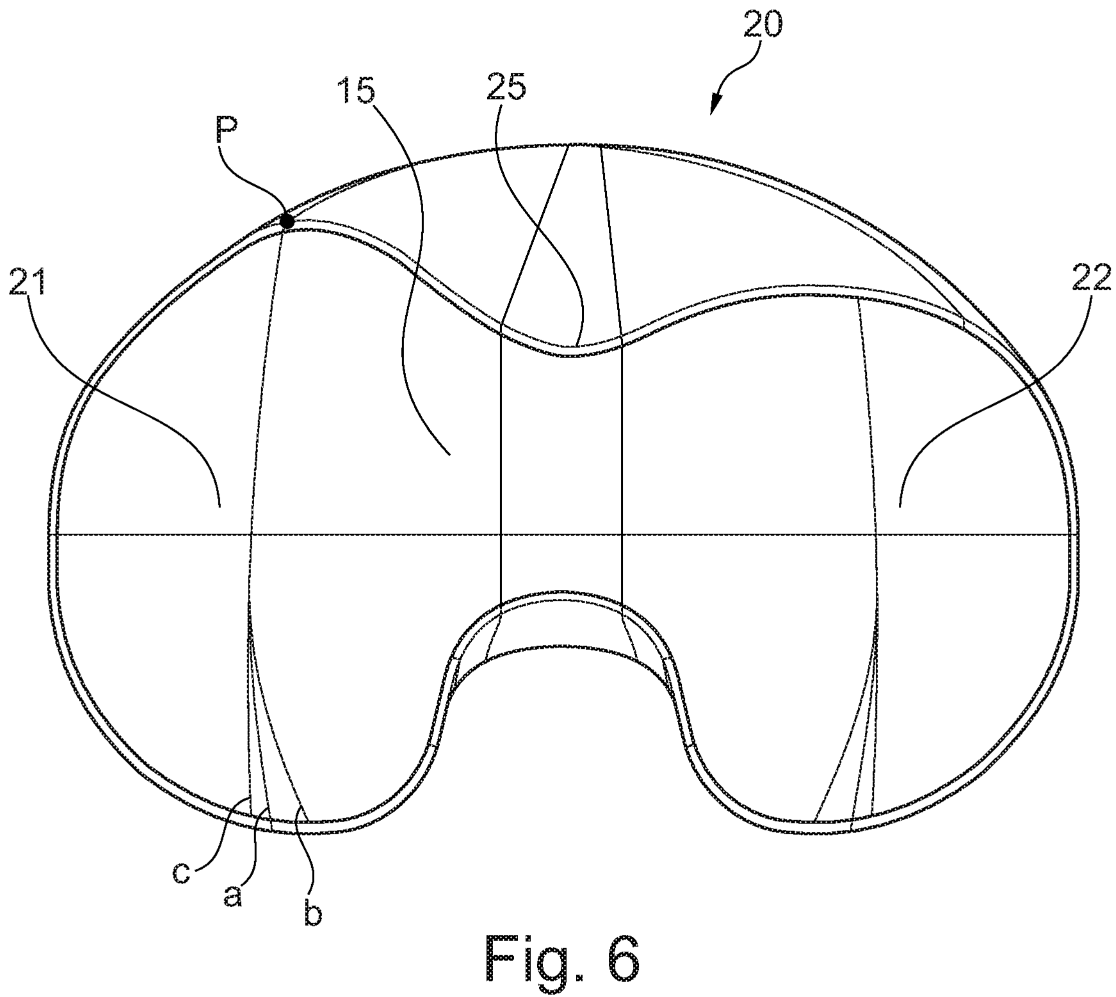
FIG. 6 is a top view of the inlay of the knee endoprosthesis according to the embodiment, viewed from a proximal viewpoint, in a viewing direction towards distally onto the inlay (or, respectively, onto the upper side of the tibia part), especially for illustration of three variants of a respective guiding curvature line, formed as a respective trajectory of a contact point between the inlay as the tibia bearing surface and the femur bearing surface.

Especially, FIG. 6, which shows a top view of the inlay 20, viewed from a proximal viewpoint, in a viewing direction towards distally onto the inlay (or, respectively, onto the upper side of the tibia part), serves to illustration of three respective independently preferred embodiments or, respectively, variants a, b, c of a respective guiding curvature line. Thereby, as guiding curvature line (of the slide bearing), the one line that maps a respective trajectory of a contact point between the (surface) area of the inlay 20 forming the tibia bearing surface 15 and the femur bearing surface 55 is designated. Variant b denotes a first guiding curvature line (more-curved), which is pronounced with the strongest radius of curvature compared to the variants of a second guiding curvature line a (slightly-curved) and a third guiding curvature line c (approximately straight). The first guiding curvature line b represents a slide bearing or, respectively, guidance of the kinematic effected according to the disclosure, in which the trajectory along its course towards posteriorly experiences a stronger bending-in towards central. With regard to the medial first guiding curvature line b, the corresponding trajectory undergoes, along its course from a central region of the medial bearing shell 21 towards posteriorly, a stronger bending-in in direction towards centrally or, respectively, laterally.

As discussed earlier, there is a tendency on the medial side to remain more or less stationary, while on the lateral side evasion movements backwards or, respectively, towards posteriorly are effected. Thus, since the distance A inlay (see FIG. 5) between the medial bearing shell 21 and the lateral bearing shell 22 is fixed, the lateral contact point will move backwards and a little inwards towards the central region of the inlay 20, or, respectively, turn towards laterally.

It has been found that especially that guiding curvature line describes an optimal trajectory that (at least in a posterior trajectory section) is drawn circularly with a radius of curvature of 76 to 78 mm, especially of ca. 77 mm, from a center of the tibia bearing surface 19. It has been shown that the aforementioned especially preferred radius of curvature, as compared to a larger or smaller radius of curvature, optimizes the mobility of the knee endoprosthesis according to the disclosure and minimizes wear thereof. Further, the lateral congruency is compensated due to this. A further advantage is that the knee is enabled to roll back (cf. Fig. map of FIG. 14). Still further, the knee's ability to rotary movements (rotation) with at the same time maximum congruency of the slide bearing is thereby important in a positive way.

FIGS. 7 or, respectively, 8 show, with reference to FIG. 5, a sagittal sectional view of a medial cross-section of the inlay 20 or, respectively, of a lateral cross-section of the inlay 20, respectively. From FIG. 7, a (tibia-side) curvature line of the medial bearing shell 21 in posterior-anterior direction can be seen. On the other hand, from FIG. 8, a curvature line of the lateral bearing shell 22 in posterior-anterior direction can be seen.

In FIG. 7 it can be seen how an anterior or, respectively, a posterior bearing height h are respectively defined in an analogous manner, namely in the sense of the depth of the medial bearing shell 21 (or, respectively, of the depth of the lateral bearing shell 22) when measured from the anterior elevation point H-ant or, respectively, from the posterior elevation point H-post as an upper (proximal) bearing shell edge.

The posterior elevation point H-post (see FIG. 5), which is located in the medial sagittal plane of FIG. 7, forms a posterior bearing height h. Thereby, the posterior bearing height is related to a proximally lowest (i.e. proximally least elevated) bearing low point T in the concave medial bearing shell 21. The anterior elevation point H-ant (see FIG. 5), which lies in the medial sagittal plane of FIG. 7, forms an anterior bearing height h (without reference sign). Thereby, the anterior bearing height, just like already the posterior bearing height h, is related to the bearing low point T. According to the feature already discussed with reference to FIGS. 4 and 5 that the anterior elevation contour portion, especially of the medial bearing shell 21, is drawn higher (more proximally) than the posterior elevation contour portion, the anterior bearing height turns out to be greater than the posterior bearing height h. Further, the maximum anterior bearing height is formed at the antero-medial apex point P (cf. FIG. 5).

As viewed in FIG. 7 for its medial sagittal plane, in the medial bearing shell 21, the anterior bearing height spans a pitch triangle from the anterior elevation point H-ant to the proximally lowest bearing low point T (as a vertex of the pitch triangle). Thereby, the pitch triangle forms a medial pitch angle β-med disposed at the bearing low point. The medial pitch angle β-med provided in FIG. 7 measures ca. 22 degrees. Thus, the desired antero-medial stabilization in the artificial knee joint is optimally further supported.

As viewed in FIG. 7 (medial sagittal plane), the medial bearing shell 21 has a first anterior surface portion which is concavely curved with an antero-medial tibia bearing surface radius R1-med/ant as a first radius. In addition, the medial bearing shell 21 has a posterior surface portion which is curved with a postero-medial tibia bearing surface radius R2-med/post as a second radius differently concave thereto. Thereby, the postero-medial tibia bearing surface radius R2-med/post is smaller than the antero-medial tibia bearing surface radius R1-med/ant.

The antero-medial tibia bearing surface radius R1-med/ant corresponds to an anterior femur condylar radius R3 of the femur part (see FIG. 11*a*). Thereby, the anterior femur condylar radius R3 may preferably be selected according to the femur radius of a natural or, respectively, representative femur condyle according to a specific femur size class.

The postero-medial tibia bearing surface radius R2-med/post corresponds to a posterior femur condylar radius R4 of the femur part (see FIG. 11*a*). Thereby, the posterior femur condylar radius R4 may preferably be selected according to the femur radius of a natural or, respectively, representative femur condyle according to a specific femur size class.

Figure 8:
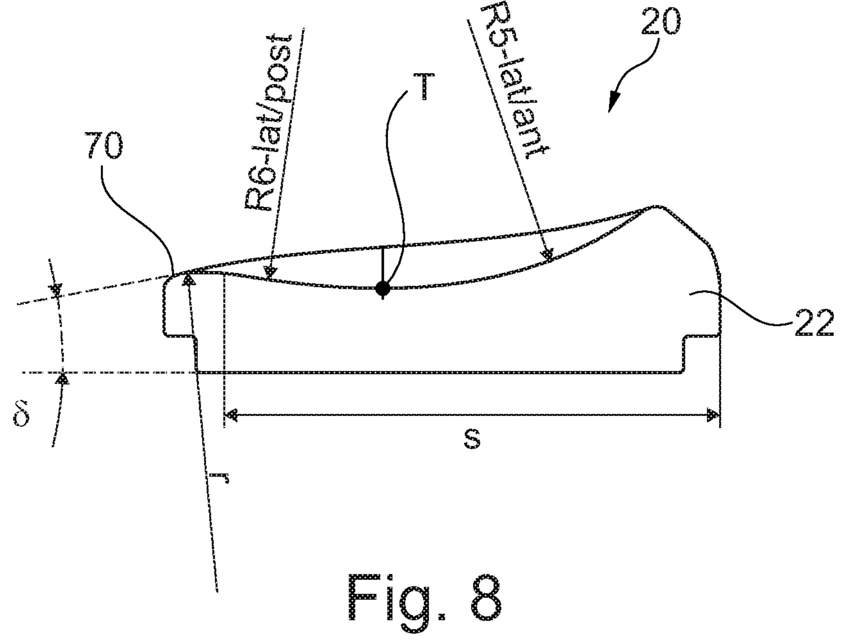
FIG. 8 is, with reference to FIG. 5, a sectional view of the lateral cross-section of the inlay of the knee endoprosthesis according to the embodiment, especially for illustration of a curvature line of the lateral bearing shell in posterior-anterior direction.

As shown in FIG. 8 (lateral sagittal plane), the lateral bearing shell 22 has an anterior surface portion which is concavely curved with an antero-lateral tibia bearing surface radius R5-lat/ant as a fifth radius. In addition, the lateral bearing shell 22 has a posterior surface portion which is curved with a postero-lateral tibia bearing surface radius R6-lat/post as a sixth radius differently concavely thereto. Thereby, the postero-lateral tibia bearing surface radius R6-lat/post is greater than the antero-lateral tibia bearing surface radius R5-lat/ant.

Figure 11B:
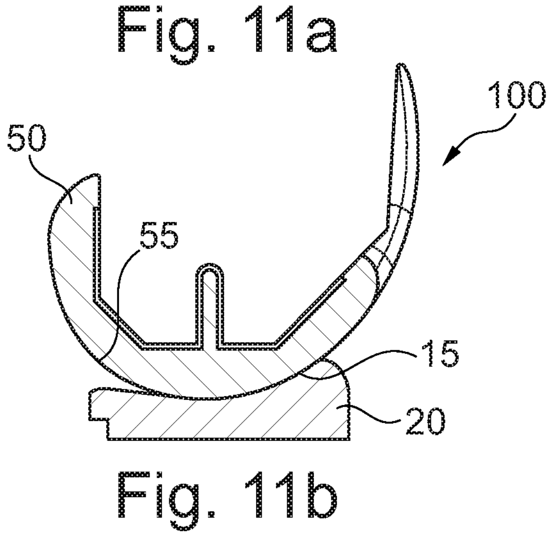
Figure 11C:
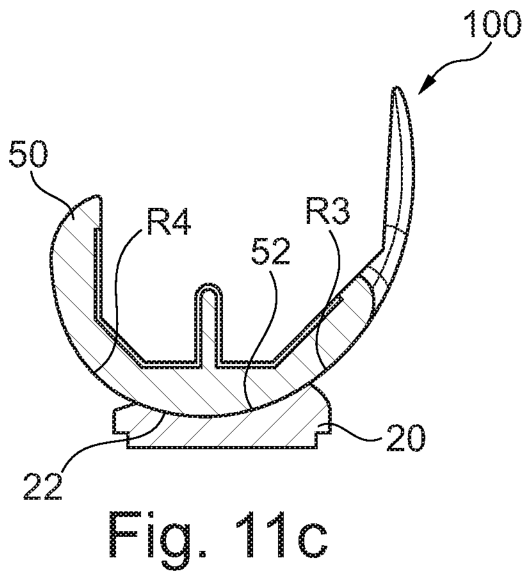

The antero-lateral tibia bearing surface radius R5-lat/ant corresponds to the anterior femur condylar radius R3 of the femur part (see FIG. 11*c*).

The postero-lateral tibia bearing surface radius R6-lat/post is formed larger in comparison to the posterior femur condylar radius R4 (see FIG. 11*c*) in order to, according to the disclosure, form a postero-laterally reduced congruency. For this purpose, the tibia bearing surface radius R6-lat/post is 80 mm.

As FIG. 7 further shows, a postero-medial phase 60 extending obliquely towards distally from the posterior elevation point H-post is provided at the medial bearing shell 21. The postero-medial phase 60 serves to the peripheral material subtraction from the medial bearing shell 21 in order to mitigate a conflict of the bone with the medial bearing shell 21 potentially occurring postero-medially during strong flexion. In the sagittal plane of the sheet of FIG. 7, the postero-medial phase 60 is at a posterior phase angle δ to a transverse plane (e.g., a flat bottom plate of the inlay 20). The postero-medial phase 60 is chamfered with a posterior phase angle δ of ca. 35 degrees.

As FIG. 8 further shows, a postero-lateral phase 70 extending obliquely towards distally at the posterior elevation point H-post is at the lateral bearing shell 22. Like already the postero-medial phase 60, the postero-lateral phase 70 also serves for peripheral material subtraction. In the sagittal plane of the sheet of FIG. 8, the postero-lateral phase 70 is at a posterior phase angle δ to a transverse plane. Thereby, the posterior phase angle δ measures ca. 10 degrees. Further, the postero-lateral phase 70 is rounded with a postero-lateral curvature radius r of ca. 12 mm. In this respect, the postero-lateral phase 70 shortens the congruent part of the posterior surface portion with the postero-lateral tibia bearing surface radius R6-lat/post, which is referred to as line-bearing portion s. The line-bearing portion s is 90% of the clear width of the inlay 20 along a sagittal axis, measured from the anterior body edge of the inlay 20.

FIGS. 9 and 10 show a first and a second perspective view of the femur part 50 according to the embodiment of the knee endoprosthesis according to the present disclosure. Thereby, FIG. 9 is viewed from a posterior viewpoint. FIG. 10 shows the perspective rotated in space relative to FIG. 9 when viewed from an obliquely distal viewpoint and in a viewing direction onto the femur bearing surface oriented towards distally or, respectively, against the underside of the femur part 50. It is apparent from the FIGS. 9 and 10, as already described in connection with FIG. 1, that the medial femur condylar bearing surface 51 and the lateral femur condylar bearing surface 52, as two (essentially) identically shaped regions of the femur bearing surface, form the latter symmetrically.

As can be further seen especially from FIG. 9, the shaping in the anterior cap-shaped portion of the femur part 50, which appears as rounded triangle, is irrelevant for the assessment of the feature of a non-asymmetric, especially of, with respect to a sagittal plane, an axisymmetric, femur bearing surface. In this respect, the comparison of the medial femur condylar bearing surface 51 and of the lateral femur condylar bearing surface 52, which function as femur bearing surface, must be taken into account. In other words, those surface areas are relevant as femur bearing surface that form a (functionally intended) contact zone with the tibia bearing surface provided for the formation of the slidable slide bearing (during regular flexion). Details on the topic of the contact zone or, respectively, congruency can be seen in FIGS. 11*a* to 11*c* discussed in the following.

FIGS. 11*a* to 11*c* show respective sectional views of the knee endoprosthesis according to the embodiment, along the posterior-anterior direction (i.e. in a sagittal plane; posterior in each case on the left in FIG. 11). Namely, with reference to the section lines drawn in FIG. 5, these concern the medial cross-section (FIG. 11*a*), the central cross-section (FIG. 11*b*), and the lateral cross-section (FIG. 11*c*). Thereby, the situation is shown with a stretched knee endoprosthesis (i.e. at a flexion angle of approximately zero angular degrees).

The three cross-sections shown here are relevant with regard to the formation of the slidable slide bearing from the femur part 50 supported on the inlay 20. Thus, the high congruency of the tibia-side curvature line of the inlay 20 (as discussed above with reference to FIG. 7 for the medial cross-section and with reference to FIG. 8 for the lateral cross-section) to a femur-side curvature line of the femur part 50 is apparent from this.

As FIG. 11*a* (medial sagittal plane) shows, the medial femur condylar bearing surface 51 has an anterior surface portion which is convexly curved with an anterior femur condylar radius R3 as a third radius. Sagittally opposite, the medial femur condylar bearing surface 51 has a posterior surface portion which is convexly curved with a posterior femur condylar radius R4 as a fourth radius.

In the FIGS. 11*a* to 11*c*, the femur part 50 is formed with the anterior femur condylar radius R3 and the posterior femur condylar radius R4 in a preferable manner such that these are predetermined to fit for a specific femur size class for a patient. Thus, the anterior femur condylar radius R3 corresponds to the anterior femur radius of a natural or, respectively, representative femur condyle according to the specific femur size class, while the posterior femur condylar radius R4 corresponds to the posterior femur radius according to the specific femur size class.

In the extension position (0 degree flexion angle) shown in FIG. 11*a*, there is a high congruency, especially clearance fit, of the medial bearing shell 21 of the inlay 20, as discussed in detail with reference to FIG. 7, to the femur part 50 being supported on the medial bearing shell 21 in a slide-bearing manner.

As FIG. 11*c* (lateral sagittal plane) shows, the lateral femur condylar bearing surface 52 has an anterior or, respectively, posterior surface portion, which-due to the symmetry of the femur bearing surface-is convexly curved also with the anterior femur condylar radius R3 (third radius) or, respectively, with the posterior femur condylar radius R4 (fourth radius), according to the femur size class. Thereby, the lateral femur condylar bearing surface 52 is slide-bearing-supported at the lateral bearing shell 22 of the inlay 20 discussed in detail with reference to FIG. 8. From the shown extension position (0 degree flexion angle) the (especially anterior) congruency can be seen.

Figures 12A, 12B, 12C, 12D:
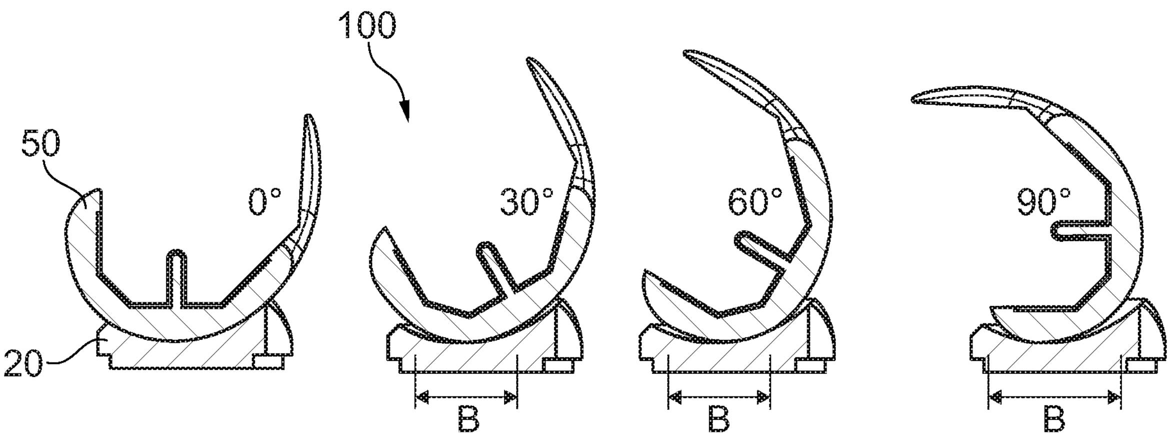
FIGS. 12*a* to 12*d*, in contrast to the FIGS. 13*a* to 13*d* for the state of the art, show respective sectional views of the knee endoprosthesis according to the embodiment, along the posterior-anterior direction, for four respective flexion angles at ca. 0° (zero angular degrees, stretched), at ca. 30°, at ca. 60° or, respectively, at ca. 90° flexion, for illustration of the movement development according to the disclosure (especially with respect to a quasi-symmetric femur bearing surface, further with respect to an especially preferred multi-radii design variant of the tibia-side curvature line)
Figures 13A, 13B, 13C, 13D:
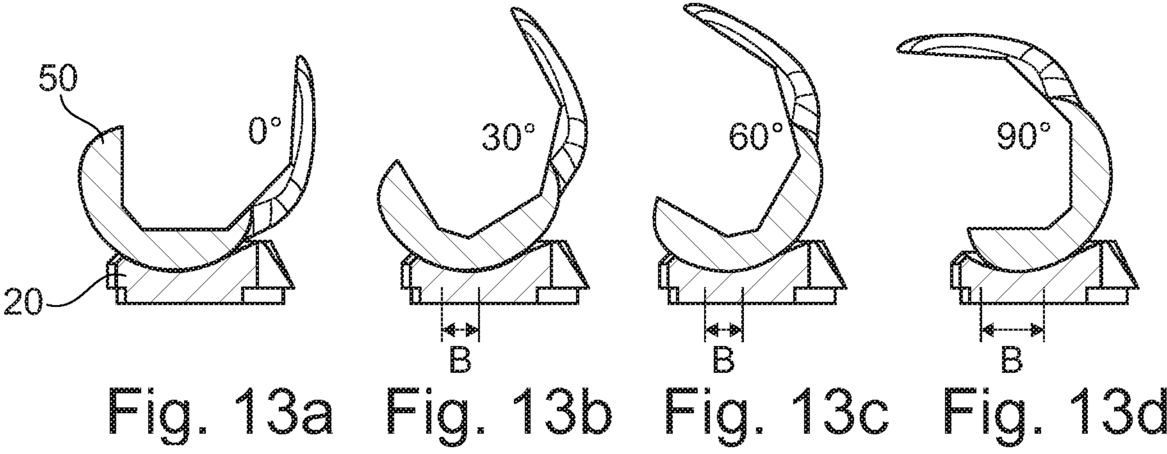
FIGS. 13*a* to 13*d* show respective sectional views of a knee endoprosthesis according to the state of the art, along the posterior-anterior direction, for four respective flexion angles at ca. 0° (zero angular degrees, stretched), at ca. 30°, at ca. 60° or, respectively, at ca. 90° flexion, for illustration of the movement development of a previously known medially stable knee endoprosthesis or, respectively, of a medial-pivot design (esp. with respect to an asymmetric femur bearing surface and a tibia-side curvature line having a constant radius)

FIGS. 12*a* to 12*d* of the present disclosure show, in contrast to the FIGS. 13*a* to 13*d* showing the state of the art, respective sectional views of the knee endoprosthesis 100 according to the embodiment, along the posterior-anterior direction. Thereby, the knee endoprosthesis 100 includes the inlay 20 (see FIGS. 2 to 7) in interaction with the femur part 50 (see FIGS. 8 and 9). From the sequential illustration, the kinematic behavior during knee flexion can be seen for four respective flexion angles, starting from at ca. 0° (FIG. 12*a*) corresponding to a stretched leg, through medium flexion at ca. 30° (FIG. 12*b*), at ca. 60° (FIG. 12*c*), and up to ca. 90° (FIG. 12*d*) flexion corresponding to a perpendicularly bent knee. FIGS. 12*a* to 12*d* thus illustrate a movement development according to the disclosure, especially with regard to the effect of a quasi-symmetric femur bearing surface, further with regard to an especially preferred multi-radii design variant of the tibia-side curvature line. In the sequence of FIGS. 12*b* to 12*d*, a range of movement B according to the disclosure is indicated as a respective double arrow. From this, it can be seen that such one is present in a positive manner over a large portion of a sagittal width of the knee endoprosthesis 100. Further, an especially high flexibility in the sense of an even further increased range of movement B at ca. 90° flexion can be seen. The kinematic properties shown here support athletic courses of movement.

FIGS. 13*a* to 13*d* show, in analogy to FIGS. 12*a* to 12*d* discussed above, corresponding respective sectional views of a knee endoprosthesis according to the state of the art. FIGS. 13*a* to 13*d* thus illustrate a conventional movement development of a previously known medially stable knee endoprosthesis or, respectively, of a medial-pivot design. It can be seen from the range of movement B, designated as respective double arrow, which is dimensioned at ca. 30° (FIG. 13*b*), at ca. 60° (FIG. 13*c*) or, respectively, at ca. 90° (FIG. 13*d*) flexion angle, that this is slight or, respectively, narrowly limited in the state of the art. Thereby, the conventionally narrow range of movement is due to the medial-pivot design with an asymmetric femur bearing surface and a tibia side curvature line having a constant radius.

Figure 14:
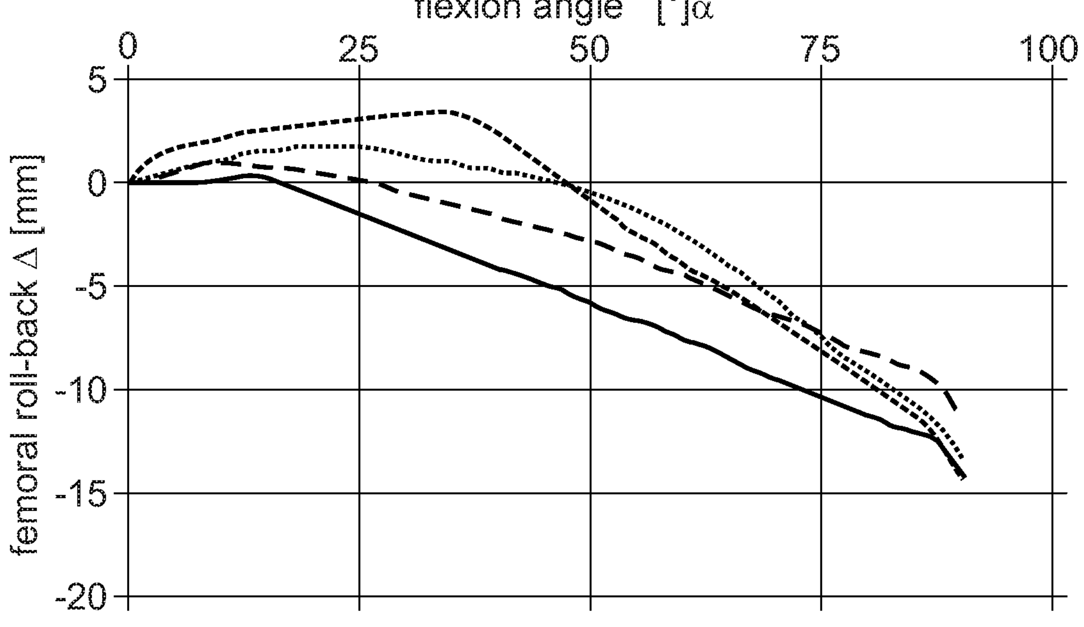
FIG. 14 shows a characteristic diagram with four kinematic characteristic lines for illustration of the influence of different shape designs of a tibia bearing surface and a femur bearing surface for the joint formation of a respective slide bearing, namely for comparison of a further preferred embodiment of a knee endoprosthesis according to the present disclosure versus three previously known knee endoprostheses from the state of the art (or, respectively, products available on the market from three manufacturers), shown as respective dependencies of the femur "roll-back" in a range from ca. 0° to ca. 90° flexion angle, as determined by means of kinematic finite element simulation.

FIG. 14 shows a characteristic diagram with four kinematic characteristic lines for comparative illustration of the influence of different shape designs of a tibia bearing surface and a femur bearing surface for the joint formation of a respective slide bearing. In the characteristic diagram, the influence of the flexion angle $\alpha$ on the femoral roll-back $\Delta$ is shown. Thereby, the femoral roll-back A is shown in form of negative values (negative value range), insofar as this relates to a backward movement. In other words, a positive y-value for the femoral roll-back in the characteristic diagram vice versa indicates a roll-front movement. Thereby, the respective characteristic lines were equally determined in a range from ca. 0° to ca. 90° flexion angle using a kinematic simulation method based on finite element calculations. Thereby, a situation without posterior cruciate ligament was simulated, respectively.

On the one hand, a further preferred embodiment of a knee endoprosthesis according to the disclosure is shown, according to the present disclosure, by means of the continuously-drawn characteristic line. On the other hand, three characteristic lines for different previously known knee endoprostheses from the state of the art are compared, which relate to products available on the market from three manufacturers.

FIG. 14 shows that with all three previously known knee endoprostheses differently high levels of the roll-front movement are effected in the initial flexion, insofar as they still exhibit positive y-values up to ca. 30° or, respectively, ca. 45° flexion angle. Thereby, the three broken characteristic lines show the previously known knee endoprostheses, in order from top to bottom in FIG. 14, as follows: an endoprosthesis marketed under the registered trademark PFC SIGMA® (from manufacturer J. & J), an endoprosthesis marketed under the registered trademark COLOMBUS® (from Aesculap), and an endoprosthesis marketed under the registered trademark ATTUNE® (from Depuy). Only with further increase of the flexion angle above this, can the roll-back (negative values) desired for emulating natural sporting courses of movement take place with the three previously known knee endoprostheses.

In contrast, for the further preferred embodiment according to the present disclosure, the continuously-drawn characteristic line proves that this significantly and in an advantageous manner differs from the state of the art. Thus, there is a minimal occurrence of roll-front (positive range of values) in the early flexion to be noted, even in the situation without posterior cruciate ligament, as well as a very good (linear) rolling-back in the further flexion.

As plotted in the characteristic diagram of FIG. 14, in the knee endoprosthesis of the further preferred embodiment, a femoral roll-back is caused. The femoral roll-back (recognizable as values in the negative range, since related to roll-front axis, i.e. to a coordinate axis positive in forward direction) is less than or equal to minus 1.5 mm at 30 degrees or, respectively, less than or equal to minus 6 mm at 60 degrees or, respectively, less than or equal to minus 11 mm at a flexion angle of ca. 90 degrees. Accordingly, this means that an amount value of the femoral roll-back is preferably greater than or equal to 1.5 mm at 30 degrees and/or greater than or equal to 6 mm at 60 degrees and/or greater than or equal to 11 mm at ca. 90 degrees flexion angle.

Further, it can be seen from the characteristic line according to the disclosure of the further preferred embodiment that in a reversal range at ca. 14 degrees of flexion angle, the femural movement changes from an (anyway minimal) roll-front into a roll-back (the amount value of which increasing further on). Until the reaching of the reversal range at ca. 14 degrees of flexion angle, i.e. in the low or, respectively, early flexion, the femural roll-front is less than or equal to ca. 0.5 mm.

These results from the characteristic diagram of FIG. 14 confirm that a complete congruency is not necessary to ensure a stability in the early flexion. And by the deviating, in accordance with the disclosure, from an a complete congruency, it can be advantageously achieved that this does not adversely oppose the desired femoral roll-back in the further flexion or, respectively, suppress it.

The invention claimed is:

1. A knee endoprosthesis for total knee arthroplasty with preservation or with dissection of a posterior cruciate ligament, the knee prosthesis comprising:

a femur part with a femur bearing surface, the femur part configured for fixation to a distal end of a femur with the femur bearing surface oriented distally; and a tibia part with a tibia bearing surface, the tibia part configured for fixation to a proximal end of a tibia with the tibia bearing surface oriented proximally, the femur bearing surface having a convex medial femur condylar bearing surface and a convex lateral femur condylar bearing surface, the tibia bearing surface having a concave medial bearing shell and a concave lateral bearing shell, the tibia bearing surface configured for accommodation and slidable on a slide bearing of the femur bearing surface without a fixed medial pivot of the femur bearing surface in the medial bearing shell, the medial bearing shell forming an asymmetric tibia bearing surface with the lateral bearing shell, the medial femur condylar bearing surface forming a non-asymmetric or quasi-symmetric femur bearing surface with the lateral femur condylar bearing surface, the medial femur condylar bearing surface and the lateral femur condylar bearing surface coinciding at least in an anterior femur condylar radius of respective anterior surface portions, the asymmetric tibia bearing surface forming an outside circumferential proximal elevation contour, the outside circumferential proximal elevation contour having an anterior elevation contour portion with at least one anterior elevation point and a posterior elevation contour portion with at least one posterior elevation point, the anterior elevation point is being proximally elevated relative to the posterior elevation point with respect to at least one sagittal plane, and an antero-medial elevation contour portion of the anterior elevation contour portion at the medial bearing shell forming a proximally most elevated anterior elevation point as an antero-medial apex point.

2. The knee endoprosthesis according to claim 1, wherein:

the anterior elevation point forms, with respect to a sagittal plane, an anterior bearing height with respect to a proximally lowest bearing low point in the concave medial and/or lateral bearing shell, the posterior elevation point, with respect to a sagittal plane, forms a posterior bearing height with respect to a proximally lowest bearing low point in the concave medial and/or lateral bearing shell, and the anterior bearing height is greater than the posterior bearing height.

3. The knee endoprosthesis according to claim 2, wherein:

in a medial sagittal plane, a pitch triangle spanning from the anterior elevation point with the anterior bearing height to the proximally lowest bearing low point in the medial bearing shell forms a medial pitch angle located at the proximally lowest bearing low point, and the medial pitch angle measures 12 to 32 degrees.

4. The knee endoprosthesis according to claim 1, wherein:

a most distal point of the medial femur condylar bearing surface forms a medial extension bearing surface contact point which is in contact with the medial bearing shell of the tibia bearing surface at about 0 degrees of flexion angle, and the medial extension bearing surface contact point;

is located at 50 to 70 degrees when at about 0 degrees flexion angle with respect to a sagittal plane as angular segment related to an anterior edge of the medial femur condylar bearing surface; and/or is located at 55 to 75 degrees when at about 0 degrees flexion angle with respect to a sagittal plane as angular segment related to an anterior edge of the medial bearing shell of the tibia bearing surface.

5. The knee endoprosthesis according to claim 1, wherein:

the concave medial bearing shell, with respect to a medial sagittal plane, has at least one anterior surface portion having a first radius forming an antero-medial tibia bearing surface radius, and at least one posterior surface portion having a second radius different from the first radius, forming a postero-medial tibia bearing surface radius.

6. The knee endoprosthesis according to claim 1, wherein the concave lateral bearing shell forms, with respect to a lateral sagittal plane, at least one anterior surface portion having a fifth radius forming an antero-lateral tibia bearing surface radius and at least one posterior surface portion having a sixth radius different from the fifth radius, forming a postero-lateral tibia bearing surface radius.

7. The knee endoprosthesis according to claim 1, wherein:

at the medial bearing shell, a postero-medial phase extending obliquely towards distally from the posterior elevation point is provided for peripheral material substraction, which, when projected in a sagittal plane, is at a posterior phase angle to a transverse plane, and the postero-medial phase is chamfered with a posterior phase angle from 30 to 40 degrees.

8. The knee endoprosthesis according to claim 1, wherein:

at the lateral bearing shell, a postero-lateral phase extending obliquely towards distally at the posterior elevation point for peripheral material substraction is provided, which, when projected in a sagittal plane, is at a posterior phase angle to a transverse plane, and the postero-lateral phase is formed with a posterior phase angle from 5 to 15 degrees, and/or is rounded with a postero-lateral curvature radius from 10 to 14 mm.

9. The knee endoprosthesis according to claim 1, wherein:

the tibia bearing surface forms an anterior patella bulge, provided centrally between the medial bearing shell and the lateral bearing shell, with a concave outer body contour.

10. The knee endoprosthesis according to claim 1, wherein the medial femur condylar bearing surface and the lateral femur condylar bearing surface form a femur bearing surface that is axisymmetric with respect to a sagittal plane disposed between the medial femur condylar bearing surface and the lateral femur condylar bearing surface.

11. The knee endoprosthesis according to claim 1, wherein:

the medial femur condylar bearing surface has, at least in a distal-medial surface portion, a medial femur condylar bearing surface radius, remaining constant, the lateral femur condylar bearing surface has, at least in a lateral-medial surface portion, another lateral femur condylar bearing surface radius, remaining constant, and the medial femur condylar bearing surface radius and the lateral femur condylar bearing surface radius differ slightly from each other maximally by a ratio factor from 0.8 to 1.2.

12. The knee endoprosthesis according to claim 1, wherein the tibia bearing surface is configured for accommodation and slidable slide bearing of the femur bearing surface along a guiding curvature line formed by a plurality of contact points, so that during a flexing bending of the knee endoprosthesis, from 0 degrees to about 90 degrees flexion angle:

an amplitude from minus 0 mm to minus 11 mm femoral roll-back is effected.

13. The knee endoprosthesis according to claim 1, wherein the tibia bearing surface is configured for accommodation and slidable slide bearing of the femur bearing surface, so that during a flexing bending of the knee endoprosthesis under a gait cycle:

a medial movement of the medial femur condyle by delta 1 mm to 4 mm is effected, and a lateral movement of the lateral femur condyle by delta 6 mm to 11 mm is effected.

14. An inlay which is proximally arranged at a tibia part of a knee endoprosthesis according to claim 1, wherein:

a proximal surface of the inlay forms the tibia bearing surface having a concave medial bearing shell and a concave lateral bearing shell, which is configured for accommodation and slidable slide bearing of the femur bearing surface having a convex medial femur condylar bearing surface and a convex lateral femur condylar bearing surface without a fixed medial pivot of the femur bearing surface in the medial bearing shell, the medial bearing shell forms an asymmetric tibia bearing surface with the lateral bearing shell, the medial femur condylar bearing surface and the lateral femur condylar bearing surface form a femur bearing surface that is non-asymmetric, the medial femur condylar bearing surface and the lateral femur condylar bearing surface coincide at least in an anterior femur condylar radius of respective anterior surface portions, the asymmetric tibia bearing surface forms an outside circumferential proximal elevation contour, the elevation contour has an anterior elevation contour portion with at least one anterior elevation point and a posterior elevation contour portion with at least one posterior elevation point, wherein the anterior elevation point is proximally elevated in relation to the posterior elevation point with respect to at least one sagittal plane, and an antero-medial elevation contour portion of the anterior elevation contour portion at the medial bearing shell forms a proximally most elevated anterior elevation point as an antero-medial apex point.

* * * * *